US011872007B2

(12) United States Patent
Purohit et al.

(10) Patent No.: US 11,872,007 B2
(45) Date of Patent: Jan. 16, 2024

(54) CONSOLE OVERLAY AND METHODS OF USING SAME

(71) Applicant: Auris Health, Inc., Redwood City, CA (US)

(72) Inventors: Rishi Nikhil Purohit, Fremont, CA (US); Barry Nichols Gardiner, Orinda, CA (US); Daniel T. Wallace, Santa Cruz, CA (US)

(73) Assignee: Auris Health, Inc., Redwood City, CA (US)

( * ) Notice: Subject to any disclaimer, the term of this patent is extended or adjusted under 35 U.S.C. 154(b) by 327 days.

(21) Appl. No.: 16/914,101

(22) Filed: Jun. 26, 2020

(65) Prior Publication Data

US 2020/0405420 A1 Dec. 31, 2020

Related U.S. Application Data

(60) Provisional application No. 62/868,816, filed on Jun. 28, 2019.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/74* (2016.02); *A61B 90/36* (2016.02); *B25J 9/02* (2013.01); *B25J 9/06* (2013.01); *B25J 9/1612* (2013.01)

(58) Field of Classification Search
CPC ........ A61B 2034/105; A61B 2034/107; A61B 2034/2051; A61B 2034/2059;
(Continued)

(56) References Cited

U.S. PATENT DOCUMENTS

| 4,771,262 A | 9/1988 | Reuss |
| 4,896,554 A | 1/1990 | Culver |

(Continued)

FOREIGN PATENT DOCUMENTS

| EP | 1 800 593 | 6/2007 |
| EP | 1 109 497 | 5/2009 |

(Continued)

OTHER PUBLICATIONS

Reddy et al., May 2005, p.1-53 Porcine pulmonary vein ablation using a novel robotic catheter control system and real-time integration of CT imaging with electroanatomical mapping, Hearth Rhythm, 2(5):S121.

(Continued)

*Primary Examiner* — Jeff A Burke
*Assistant Examiner* — Zachary Joseph Wallace
(74) *Attorney, Agent, or Firm* — Conley Rose, P.C.; Gayatry S. Nair

(57) ABSTRACT

Provided are systems and techniques for a medical procedure. For example, the system may include one or more robotic arms, an imaging device, a master controller, a viewer configured to render one or more digital images based on image data from the imaging device, at least one computer-readable memory having stored thereon executable instructions, and one or more processors. The one or more processors may be configured to execute the instructions to cause the system to: in a first mode of operation, cause movement of at least one of the robotic arms; and in a second mode of operation, cause the viewer to display an interactive menu and a graphical overlay on the one or more digital images.

20 Claims, 29 Drawing Sheets

(51) Int. Cl.
  *B25J 9/06* (2006.01)
  *B25J 9/02* (2006.01)
  *B25J 9/16* (2006.01)
  *A61B 90/00* (2016.01)

(58) Field of Classification Search
  CPC ...... A61B 2034/2065; A61B 2034/302; A61B 2034/742; A61B 2090/742; A61B 2090/306; A61B 2090/309; A61B 2090/372; A61B 2560/0437; A61B 34/20; A61B 34/25; A61B 34/30; A61B 34/37; A61B 34/74; A61B 90/36; A61B 90/361; B25J 9/02; B25J 9/06; B25J 9/1612
  See application file for complete search history.

(56) References Cited

U.S. PATENT DOCUMENTS

| | | |
|---|---|---|
| 5,008,528 A | 4/1991 | Duchon |
| 5,176,310 A | 1/1993 | Akiyama et al. |
| 5,280,781 A | 1/1994 | Oku |
| 5,499,632 A | 3/1996 | Hill et al. |
| 5,524,180 A | 6/1996 | Wang et al. |
| 5,526,812 A | 6/1996 | Dumoulin et al. |
| 5,762,458 A | 6/1998 | Wang et al. |
| 5,831,614 A | 11/1998 | Tognazzini et al. |
| 5,899,851 A | 5/1999 | Koninckx |
| 5,963,770 A | 10/1999 | Eakin |
| 6,007,550 A | 12/1999 | Wang et al. |
| 6,016,439 A | 1/2000 | Acker |
| 6,038,467 A | 3/2000 | De Bliek et al. |
| 6,096,004 A | 8/2000 | Meglan et al. |
| 6,425,865 B1 | 7/2002 | Salcudean et al. |
| 6,466,198 B1 | 10/2002 | Feinstein |
| 6,468,265 B1 | 10/2002 | Evans et al. |
| 6,490,467 B1 | 12/2002 | Bucholz |
| 6,516,421 B1 | 2/2003 | Peters |
| 6,690,964 B2 | 2/2004 | Bieger et al. |
| 6,856,827 B2 | 2/2005 | Seeley et al. |
| 7,206,627 B2 | 4/2007 | Abovitz |
| 7,594,925 B2 | 9/2009 | Danek |
| 8,180,114 B2 | 5/2012 | Nishihara et al. |
| 8,716,973 B1 | 5/2014 | Lammertse |
| 8,718,837 B2 | 5/2014 | Wang et al. |
| 8,971,597 B2 | 3/2015 | Zhao et al. |
| 9,241,767 B2 | 1/2016 | Prisco et al. |
| 9,283,046 B2 | 3/2016 | Walker et al. |
| 9,498,291 B2 | 11/2016 | Balaji et al. |
| 9,503,681 B1 | 11/2016 | Popescu et al. |
| 9,504,604 B2 | 11/2016 | Alvarez |
| 9,561,019 B2 | 2/2017 | Mihailescu et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,770,216 B2 | 9/2017 | Brown et al. |
| 9,788,910 B2 | 10/2017 | Schuh |
| 9,827,061 B2 | 11/2017 | Balaji et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,925,662 B1 * | 3/2018 | Jules .................. G05B 19/423 |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,028,789 B2 | 7/2018 | Quaid et al. |
| 10,080,576 B2 | 9/2018 | Romo et al. |
| 10,123,843 B2 | 11/2018 | Wong et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,206,746 B2 | 2/2019 | Walker et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,346,976 B2 | 7/2019 | Averbuch |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,675,101 B2 | 6/2020 | Walker et al. |
| 10,682,189 B2 | 6/2020 | Schuh et al. |
| 10,688,283 B2 | 6/2020 | Wong et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,820,954 B2 | 11/2020 | Marsot et al. |
| 2002/0077533 A1 | 6/2002 | Bieger et al. |
| 2002/0082612 A1 | 6/2002 | Moll et al. |
| 2002/0120188 A1 | 8/2002 | Brock et al. |
| 2002/0161280 A1 | 10/2002 | Chatenever et al. |
| 2002/0173878 A1 | 11/2002 | Watanabe |
| 2004/0047044 A1 | 3/2004 | Dalton |
| 2004/0263535 A1 | 12/2004 | Birkenbach et al. |
| 2005/0043718 A1 | 2/2005 | Madhani |
| 2005/0085714 A1 | 4/2005 | Foley et al. |
| 2005/0193451 A1 | 9/2005 | Quistgaard et al. |
| 2005/0222554 A1 | 10/2005 | Wallace et al. |
| 2006/0079745 A1 | 4/2006 | Viswanathan et al. |
| 2006/0095022 A1 | 5/2006 | Moll et al. |
| 2006/0173290 A1 | 8/2006 | Lavallee et al. |
| 2006/0200026 A1 | 9/2006 | Wallace et al. |
| 2007/0083098 A1 | 4/2007 | Stern et al. |
| 2007/0138992 A1 | 6/2007 | Prisco et al. |
| 2007/0144298 A1 | 6/2007 | Miller |
| 2007/0185486 A1 | 8/2007 | Hauck et al. |
| 2008/0027313 A1 | 1/2008 | Shachar |
| 2008/0033442 A1 | 2/2008 | Amoit |
| 2008/0082109 A1 | 4/2008 | Moll et al. |
| 2008/0097465 A1 | 4/2008 | Rollins et al. |
| 2008/0108870 A1 | 5/2008 | Wiita et al. |
| 2008/0140087 A1 | 6/2008 | Barbagli et al. |
| 2008/0183068 A1 | 7/2008 | Carls et al. |
| 2008/0183188 A1 | 7/2008 | Carls et al. |
| 2008/0306490 A1 | 12/2008 | Lakin et al. |

(56) References Cited

U.S. PATENT DOCUMENTS

| | | |
|---|---|---|
| 2009/0248036 A1 | 10/2009 | Hoffman et al. |
| 2009/0259230 A1 | 10/2009 | Khadem |
| 2009/0259412 A1 | 10/2009 | Brogardh |
| 2009/0326322 A1 | 12/2009 | Diolaiti |
| 2009/0326556 A1 | 12/2009 | Diolaiti et al. |
| 2010/0019890 A1 | 1/2010 | Helmer et al. |
| 2010/0039506 A1 | 2/2010 | Sarvestani et al. |
| 2010/0076263 A1 | 3/2010 | Tanaka |
| 2010/0121269 A1 | 5/2010 | Goldenberg |
| 2010/0125284 A1 | 5/2010 | Tanner et al. |
| 2010/0161129 A1 | 6/2010 | Costa et al. |
| 2010/0204613 A1 | 8/2010 | Rollins et al. |
| 2010/0225209 A1 | 9/2010 | Goldberg |
| 2010/0328455 A1 | 12/2010 | Nam et al. |
| 2011/0021926 A1 | 1/2011 | Spencer |
| 2011/0113852 A1 | 5/2011 | Prisco |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0196199 A1 | 8/2011 | Donhowe et al. |
| 2011/0235855 A1 | 9/2011 | Smith |
| 2011/0238010 A1 | 9/2011 | Kirschenman et al. |
| 2011/0248987 A1 | 10/2011 | Mitchell |
| 2011/0276058 A1 | 11/2011 | Choi et al. |
| 2011/0306873 A1 | 12/2011 | Shenai et al. |
| 2012/0059392 A1 | 3/2012 | Diolaiti |
| 2012/0071752 A1 | 3/2012 | Sewell |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0103123 A1 | 5/2012 | McInroy et al. |
| 2012/0158011 A1 | 6/2012 | Sandhu |
| 2012/0203067 A1 | 8/2012 | Higgins et al. |
| 2012/0253276 A1 | 10/2012 | Govari et al. |
| 2012/0296161 A1 | 11/2012 | Wallace et al. |
| 2012/0314022 A1 | 12/2012 | Jo |
| 2013/0018306 A1 | 1/2013 | Ludwin |
| 2013/0060146 A1 | 3/2013 | Yang et al. |
| 2013/0165854 A1 | 6/2013 | Sandhu et al. |
| 2013/0178868 A1* | 7/2013 | Roh ................ A61B 34/30 606/130 |
| 2013/0245375 A1 | 9/2013 | DiMaio et al. |
| 2013/0317519 A1 | 11/2013 | Romo et al. |
| 2014/0107666 A1 | 4/2014 | Madhani |
| 2014/0111457 A1 | 4/2014 | Briden et al. |
| 2014/0142591 A1 | 5/2014 | Alvarez et al. |
| 2014/0222204 A1 | 8/2014 | Kawashima |
| 2014/0276392 A1 | 9/2014 | Wong et al. |
| 2014/0276938 A1 | 9/2014 | Hsu et al. |
| 2014/0276940 A1 | 9/2014 | Seo |
| 2014/0277333 A1 | 9/2014 | Lewis et al. |
| 2014/0357984 A1* | 12/2014 | Wallace ............ G16H 20/40 600/424 |
| 2015/0018622 A1 | 1/2015 | Tesar et al. |
| 2015/0105747 A1 | 4/2015 | Rollins et al. |
| 2015/0157191 A1 | 6/2015 | Phee et al. |
| 2015/0224845 A1 | 8/2015 | Anderson et al. |
| 2015/0265807 A1 | 9/2015 | Park et al. |
| 2015/0290454 A1 | 10/2015 | Tyler et al. |
| 2015/0375399 A1 | 12/2015 | Chiu et al. |
| 2016/0001038 A1 | 1/2016 | Romo et al. |
| 2016/0026253 A1 | 1/2016 | Bradski et al. |
| 2016/0059412 A1 | 3/2016 | Oleynik |
| 2016/0098095 A1 | 4/2016 | Gonzalez-Banos et al. |
| 2016/0183841 A1 | 6/2016 | Duindam et al. |
| 2016/0213436 A1 | 7/2016 | Inoue |
| 2016/0213884 A1 | 7/2016 | Park |
| 2016/0256069 A1 | 9/2016 | Jenkins |
| 2016/0270865 A1 | 9/2016 | Landey et al. |
| 2016/0287279 A1 | 10/2016 | Bovay et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1 | 11/2016 | Esterberg et al. |
| 2017/0007337 A1 | 1/2017 | Dan |
| 2017/0143429 A1 | 5/2017 | Richmond et al. |
| 2017/0172664 A1 | 6/2017 | Weingarten et al. |
| 2017/0180720 A1 | 6/2017 | Jarc |
| 2017/0189130 A1* | 7/2017 | Weir ................. A61B 34/37 |
| 2017/0202627 A1 | 7/2017 | Sramek et al. |
| 2017/0209073 A1 | 7/2017 | Sramek et al. |
| 2017/0282372 A1 | 10/2017 | Itkowitz et al. |
| 2017/0290631 A1 | 10/2017 | Lee et al. |
| 2018/0025666 A1 | 1/2018 | Ho et al. |
| 2018/0078321 A1 | 3/2018 | Liao |
| 2018/0079090 A1* | 3/2018 | Koenig ................ G01L 3/14 |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0090969 A1 | 3/2019 | Jarc et al. |
| 2019/0110839 A1 | 4/2019 | Rafii-Tari et al. |
| 2019/0151148 A1 | 4/2019 | Alvarez et al. |
| 2019/0151032 A1 | 5/2019 | Mustufa et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0371012 A1 | 12/2019 | Flexman |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0012116 A1* | 1/2020 | Fuerst ................ A61B 34/35 |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0138534 A1* | 5/2020 | Garcia Kilroy ...... A61G 13/101 |
| 2020/0146769 A1 | 5/2020 | Eyre |
| 2020/0163731 A1* | 5/2020 | Itkowitz ............. A61B 1/00193 |
| 2020/0170720 A1 | 6/2020 | Ummalaneni |

(56) References Cited

U.S. PATENT DOCUMENTS

| | | |
|---|---|---|
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0345432 A1 | 11/2020 | Walker |
| 2020/0352420 A1 | 11/2020 | Graetzel |
| 2020/0360183 A1 | 11/2020 | Alvarez |
| 2020/0360659 A1 | 11/2020 | Wong |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0405317 A1 | 12/2020 | Wallace |
| 2020/0405411 A1 | 12/2020 | Draper et al. |
| 2020/0405419 A1 | 12/2020 | Mao |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |
| 2021/0145526 A1* | 5/2021 | Robinson ............... A61B 34/37 |
| 2022/0218427 A1* | 7/2022 | Tomatsu ............... A61B 90/90 |

FOREIGN PATENT DOCUMENTS

| | | |
|---|---|---|
| EP | 2 158 834 | 3/2010 |
| WO | WO 08/049088 | 4/2008 |
| WO | WO 10/025522 | 3/2010 |
| WO | WO 17/214243 | 12/2017 |

OTHER PUBLICATIONS

Ren et al., 2011, Multisensor data fusion in an integrated tracking system for endoscopic surgery, IEEE Transactions on Information Technology in Biomedicine, 16(1):106-111.

International search report and written opinion dated Oct. 1, 2020 in application No. PCT/US20/39979.

Extended European Search Report; Application No. 20831751.1; dated Jun. 20, 2023; 9 pages.

* cited by examiner

CONSOLE OVERLAY AND METHODS OF USING SAME

CROSS-REFERENCE TO RELATED APPLICATION(S)

This application claims the benefit of U.S. Provisional Application No. 62/868,816, filed Jun. 28, 2019, which is hereby incorporated by reference in its entirety.

TECHNICAL FIELD

This application relates to systems and methods for performing medical procedures, and more particularly to user interfaces and controls for medical robotic systems.

BACKGROUND

Various medical procedures may be performed using a robotic medical system to control the insertion and/or manipulation of one or more medical instruments. For certain medical conditions, two or more medical procedures may be performed to treat the medical condition.

The robotic medical system may include one or more robotic arms or any other arm/instrument positioning device(s). The robotic medical system may also include a controller used to control the positioning of the instrument(s) during each of the procedures via the manipulation of the robotic arm(s) and/or arm/instrument positioning device(s).

SUMMARY

The systems, methods and devices of this disclosure each have several innovative aspects, implementations, or aspects, no single one of which is solely responsible for the desirable attributes disclosed herein.

In a first aspect, a system for a medical procedure may include a set of one or more robotic arms, an imaging device coupled to one of the set of one or more robotic arms, a master controller, a viewer communicatively coupled with the imaging device and configured to render one or more digital images based on image data from the imaging device, at least one computer-readable memory having stored thereon executable instructions, and one or more processors in communication with the at least one computer-readable memory. The one or more processor may be configured to execute the instructions to cause the system to at least, in a first mode of operation, cause movement of at least one of the set of one or more robotic arms based on a first user input received at the master controller.

The system for a medical procedure can optionally include one or more of the following features, in any combination: (a) wherein the one or more processors may be configured to execute the instructions to cause the system to, in a second mode of operation, cause the viewer to display an interactive menu and a graphical overlay on the one or more digital images; (b) wherein a second user input enables a user interaction with the menu; (c) wherein the graphical overlay comprises information regarding the procedure; (d) wherein the one or more processors are further configured to execute the instructions to generate a visual rendering of the one or more robotic arms; (e) wherein the visual rendering shows a current position and orientation of each robotic arm, and cause the viewer to display the visual rendering; (f) wherein the visual rendering includes one or more instruments or cameras associated with each of the one or more robotic arms; (g) wherein the visual rendering includes a patient's body and shows a current position and orientation of reach robotic arm relative to the patient's body; (h) wherein the visual rendering includes one or more areas of potential collision involving the one or more robotic arms; (i) wherein the potential collisions are between the one or more robotic arms; (j) wherein the system further comprises a non-robotic arm, wherein the visual rendering includes a current position and orientation of the non-robotic arm and one or more areas of potential collision between the non-robotic arm and the one or more robotic arms; (k) wherein the one or more processors are further configured to cause the viewer to display an interactive menu over at least a portion of the one or more digital images rendered in the viewer; (l) wherein the one or more processors are configured to execute the instructions to cause the viewer to display the menu at least in part over the one or more digital images; (m) wherein at least one of the one or more digital images is of a surgical site; (n) wherein the one or more processors are configured to execute the instructions to cause the viewer to display the menu completely over the one or more digital images of the surgical site; (o) wherein the one or more processors are configured to execute the instructions to cause the viewer to display the menu only partially over the one or more digital images of the surgical site in a picture in picture aspect; (p) wherein all or a portion of the menu is displayed on the viewer in both the first mode of operation and the second mode of operation, and the menu displayed on the viewer is larger in the second mode of operation than in the first mode of operation; (q) wherein the one or more processors are further configured to execute the instructions to cause the system to switch from the first mode of operation to the second mode of operation upon the receipt of a double click of a grip of the master controller; (r) wherein the one or more processors are further configured to execute the instructions to cause the system to prevent movement of one or more robotic arms when the system is in the second mode of operation; (s) wherein the system further comprises one or more foot pedals; (t) wherein the master controller comprises a first gimbal controller and a second gimbal controller; (u) wherein the one or more processors are further configured to execute the instructions to cause the system to switch from the first mode of operation to the second mode of operation upon the receipt of a simultaneous actuation of a clutch of the first gimbal controller and the second gimbal controller of the master controller and a clutch of a foot pedal; (v) wherein the one or more processors are configured to execute the instructions to, in the first mode of operation, cause movement of a first robotic arm based on a user input received at the first gimbal and cause movement of a second robotic arm based on a user input received at the second gimbal, and in the second mode of operation, cause movement of a pointer on the one or more digital images in the viewer based on a user input received at least one of the first gimbal and the second gimbal; (w) wherein the pointer interacts with the graphical overlay within the viewer; (x) wherein the user input received at one or both of the first gimbal and the second gimbal causes movement of the pointer about the menu; (y) wherein the one or more processors are further configured to execute the instructions to cause the system to switch from the first mode of operation to the second mode of operation upon the receipt of a simultaneous actuation of a clutch feature on the master controller and a clutch feature on one or more foot pedals; (z) wherein, in the second mode of operation, the one or more processors are further configured to execute the instructions to cause the system to change an association between the master controller and the first robotic arm based on a user input comprising a user interaction with at least one of the menu and the graphical overlay such that, in the first mode of operation, the one or more processors are configured to execute the instructions to cause movement of a first robotic arm based on a user input received at the second gimbal; (aa) wherein the first robotic arm is on a first side of a patient's body and the second robotic arm is on a second side of the patient's body, wherein the first side is opposite to the second side of the patient's body; (bb) wherein the viewer is a stereoscopic viewer; (cc) wherein at least one of the set of one or more robotic arms comprises a light; and/or (dd) wherein, in a second mode of operation, the one or more processors are configured to execute the instructions to actuate a light on at least one of the set of one or more robotic arms based on a user interaction with at least one of the menu and the graphical overlay.

In another aspect, a system for a medical procedure is disclosed that includes a first robotic arm, a second robotic arm, a viewer, a master controller, at least one computer-readable memory having stored thereon executable instructions, and one or more processors in communication with the at least one computer-readable memory and configured to execute the instructions to cause the system to at least, in a first state, cause movement of at least one of the set of one or more robotic arms based on user input received at the master controller and, in a second state, cause the viewer to display a visual rendering of the one or more robotic arms, wherein the visual rendering includes one or more areas of potential collision involving the first and second robotic arms.

The system for a medical procedure optionally includes one or more of the following features, in any combination: (a) wherein the system further comprises a non-robotic arm, wherein the visual rendering presents at least one image of a current position and orientation of the non-robotic arm and one or more areas of potential collision between the non-robotic arm and at least one of the first and second robotic arms; (b) wherein the system further comprises an imaging device coupled to at least one of the first and second robotic arms and communicatively coupled with the viewer; (c) wherein the visual rendering comprises a plurality of images, wherein the plurality of images show a plurality of different viewing angles of the position and the orientation of the first and second robotic arms; (d) wherein the visual rendering is a three-dimensional visual rendering of the position and the orientation of the first and second robotic arms; and/or (e) wherein the visual rendering also comprises a visual image of a position and an orientation of a patient's body.

In another aspect, a system for surgical procedures is disclosed that includes a plurality of robotic arms, a first light coupled to a first robotic arm of the plurality of robotic arms, a viewer, a master controller, at least one computer-readable memory having stored thereon executable instructions, and one or more processors in communication with the at least one computer-readable memory and configured to execute the instructions to cause the system to at least, in a first mode of operation, cause a movement of at least one of the plurality of robotic arms based on user input received at the master controller and, in a second mode of operation, activate or deactivate the first light based on a user interaction with the menu.

The system for surgical procedures optionally includes one or more of the following features, in any combination: (a) wherein the plurality of robotic arms comprises a second light coupled to a second robotic arm, wherein the one or more processors are configured to execute the instructions to cause the system to, in the second mode of operation, activate or deactivate the second light based on a user interaction with the menu; (b) wherein the first light is positioned near a distal end of the first robotic arm; (c) wherein the system further comprises an imaging device coupled to one of the plurality of robotic arms and communicatively coupled with the viewer, the viewer is configured to render one or more digital images based on image data from the imaging device; (d) wherein the one or more processors are configured to execute the instructions to cause the system to deactivate the first light upon removal of an instrument coupled with the first robotic arm; and/or (f) wherein the one or more processors are configured to execute the instructions to cause the system to deactivate the first light upon completion of an instrument exchange on the first robotic arm.

In another aspect, a method of using a robotic system having a set of one or more robotic arms adapted for surgical procedures is disclosed that includes, in a first mode of operation, causing at least one of the set of one or more robotic arms to move by generating a first user input at the master controller, viewing one or more digital images rendered on a viewer, causing the viewer to display an interactive menu over at least a portion of the one or more digital images rendered in the viewer by generating a second user input at the master controller, changing the system from the first mode of operation to a second mode of operation and, in the second mode of operation, causing the viewer to display a graphical overlay on the one or more digital images by generating a third user input at the master controller, wherein generating the third user input comprises generating a user interaction with the menu, and wherein the graphical overlay comprises information regarding the procedure.

The method of using a system having a set of one or more robotic arms adapted for surgical procedures optionally includes one or more of the following features or steps, in any combination: (a) wherein the viewer is communicatively coupled with an imaging device, the one or more digital images are based on image data from the imaging device, and the imaging device is coupled with one of the set of one or more robotic arms; (b) wherein generating the second user input at the master controller changes the system from the first mode of operation to the second mode of operation; (c) wherein changing the system from the first mode of operation to the second mode of operation comprises rapidly clicking a clutch of the master controller twice; and/or (d) wherein changing the system from the first mode of operation to the second mode of operation comprises simultaneously clicking a foot pedal and a clutch of the master controller.

In another aspect, provided is a method operable by a robotic system, the system having a master console and a set of one or more robotic arms configured to perform a medical procedure. The method may involve displaying one or more digital images on a viewer of the master console, the one or more digital images based on image data from an imaging device coupled with one of the set of one or more robotic arms. The method may further involve, in a first mode of operation, causing at least one of the set of one or more robotic arms to move in response to a first user input at a master controller of the master console. The method may further involve, in a second mode of operation, causing the viewer to display an interactive menu and a graphical overlay on the one or more digital images, wherein a second user input enables a user interaction with the menu, wherein the graphical overlay comprises information regarding the procedure.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
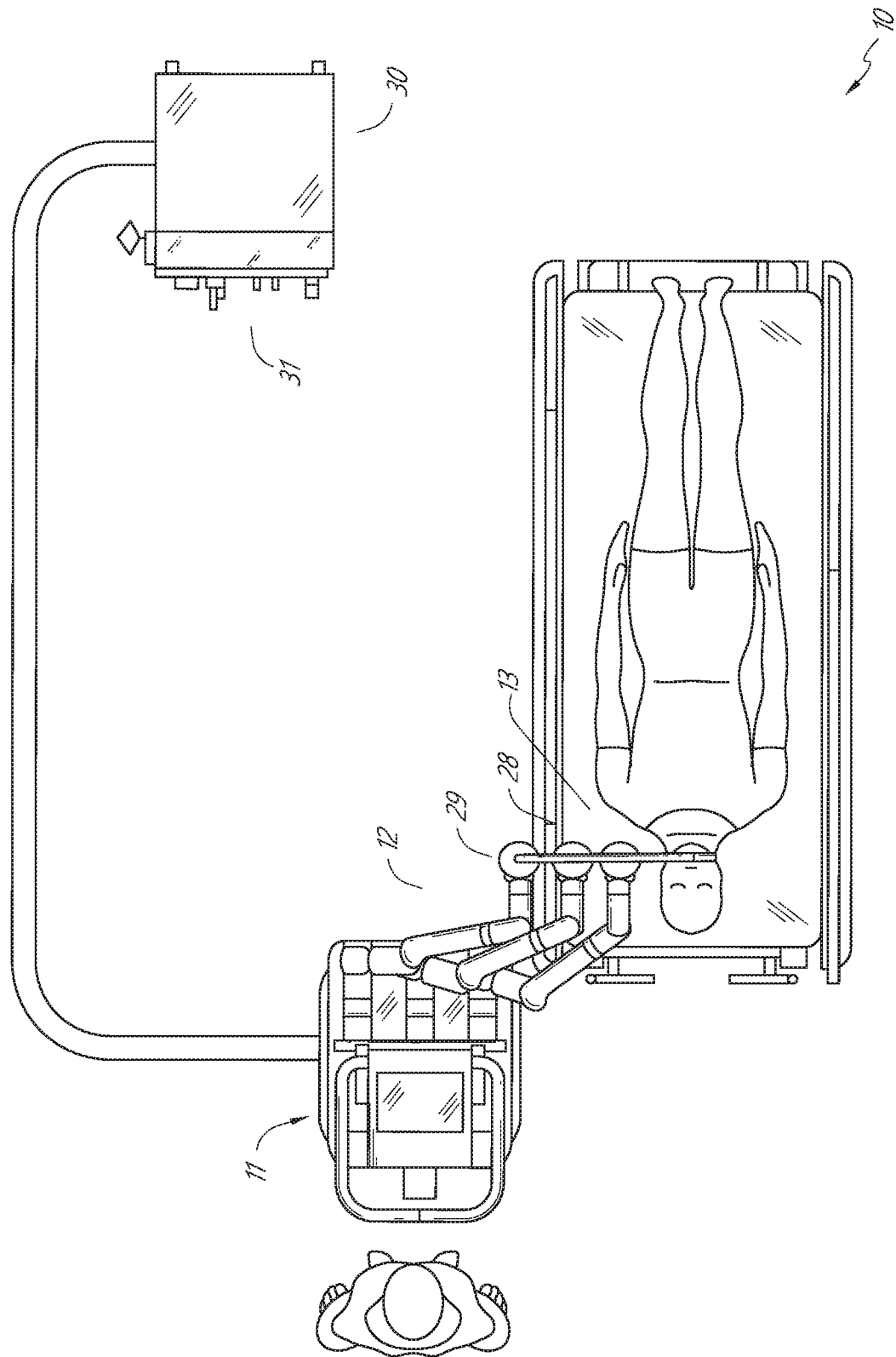
FIG. 1 illustrates an embodiment of a cart-based robotic system arranged for diagnostic and/or therapeutic bronchoscopy.
Figure 2:
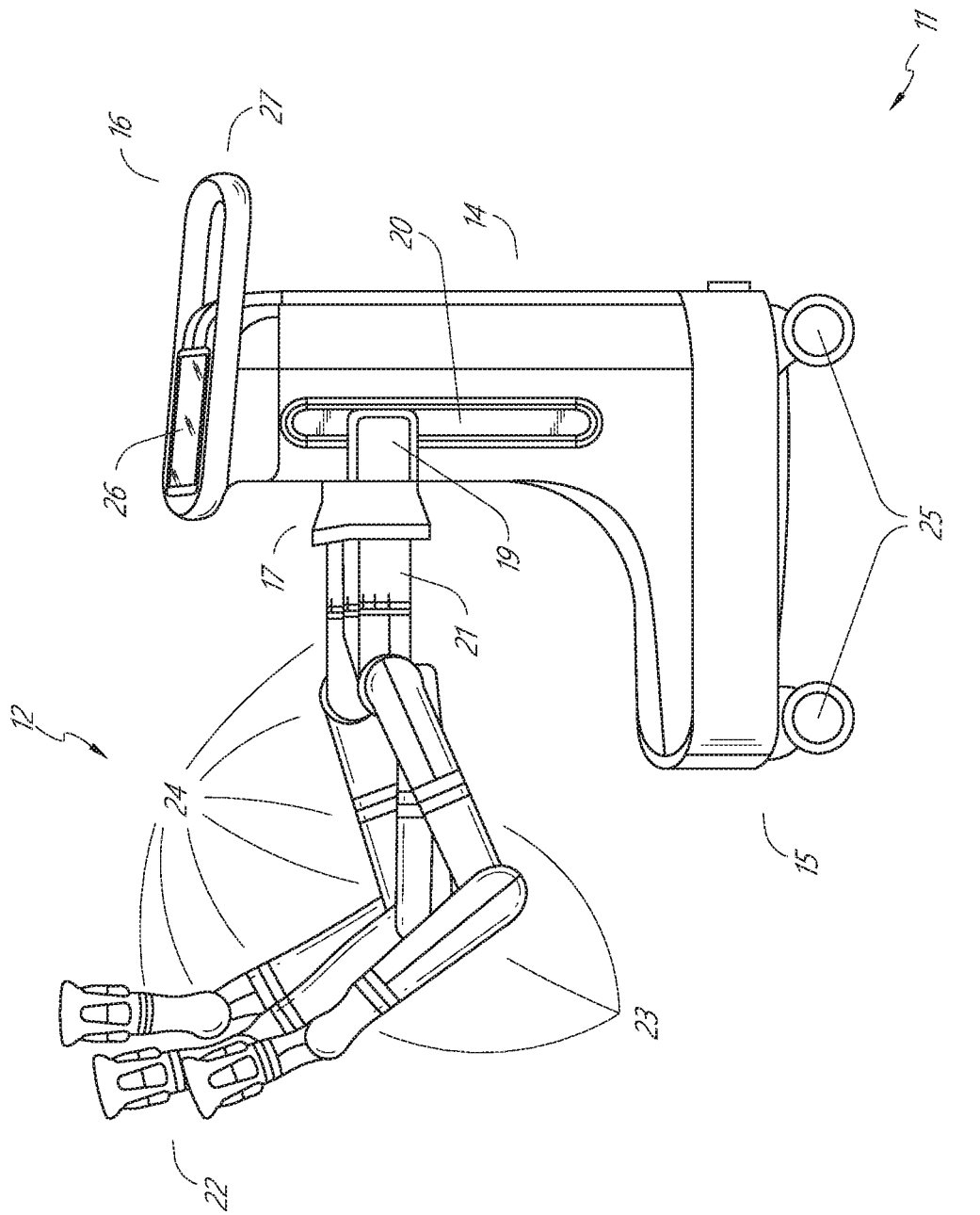
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 31 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
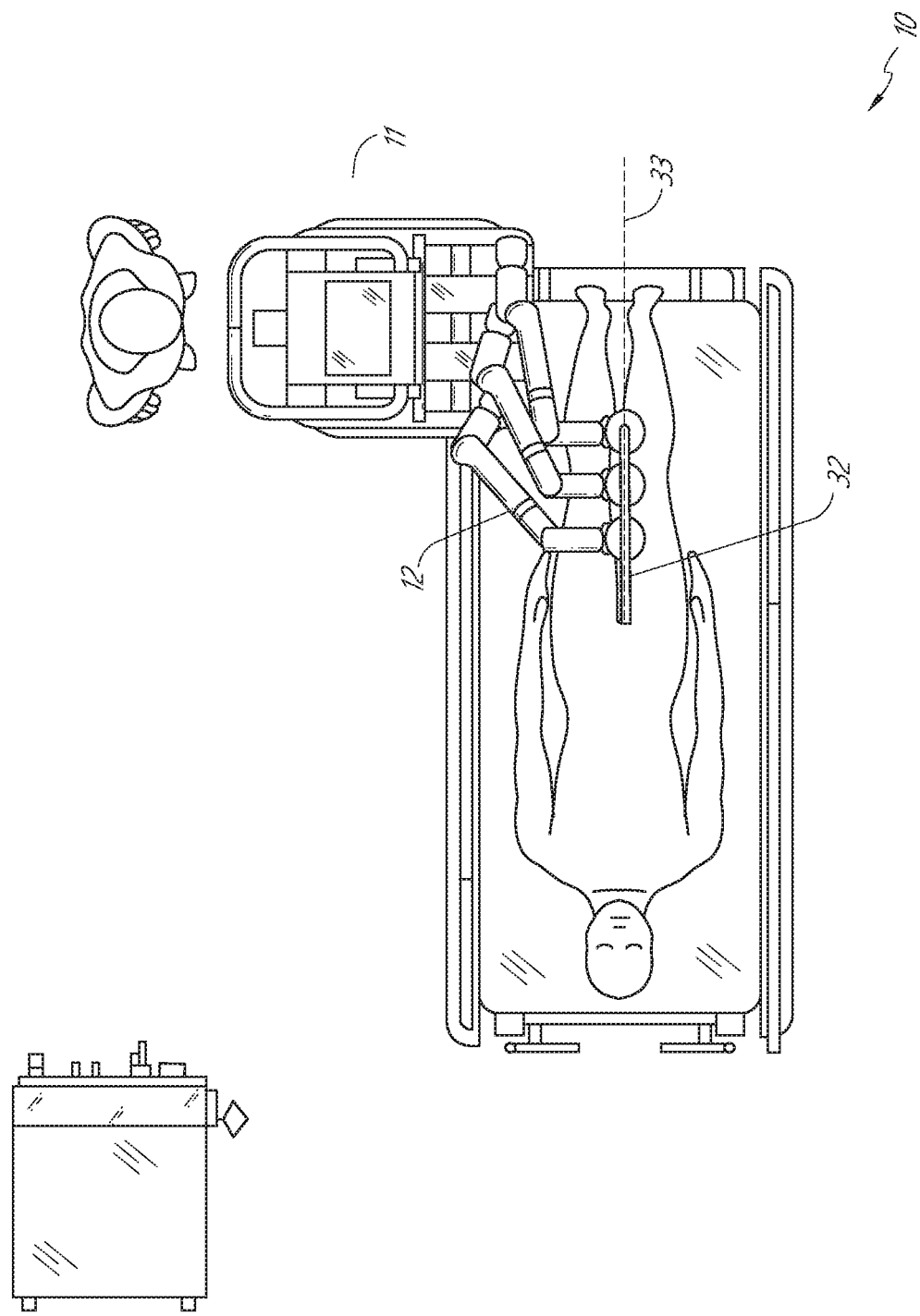
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
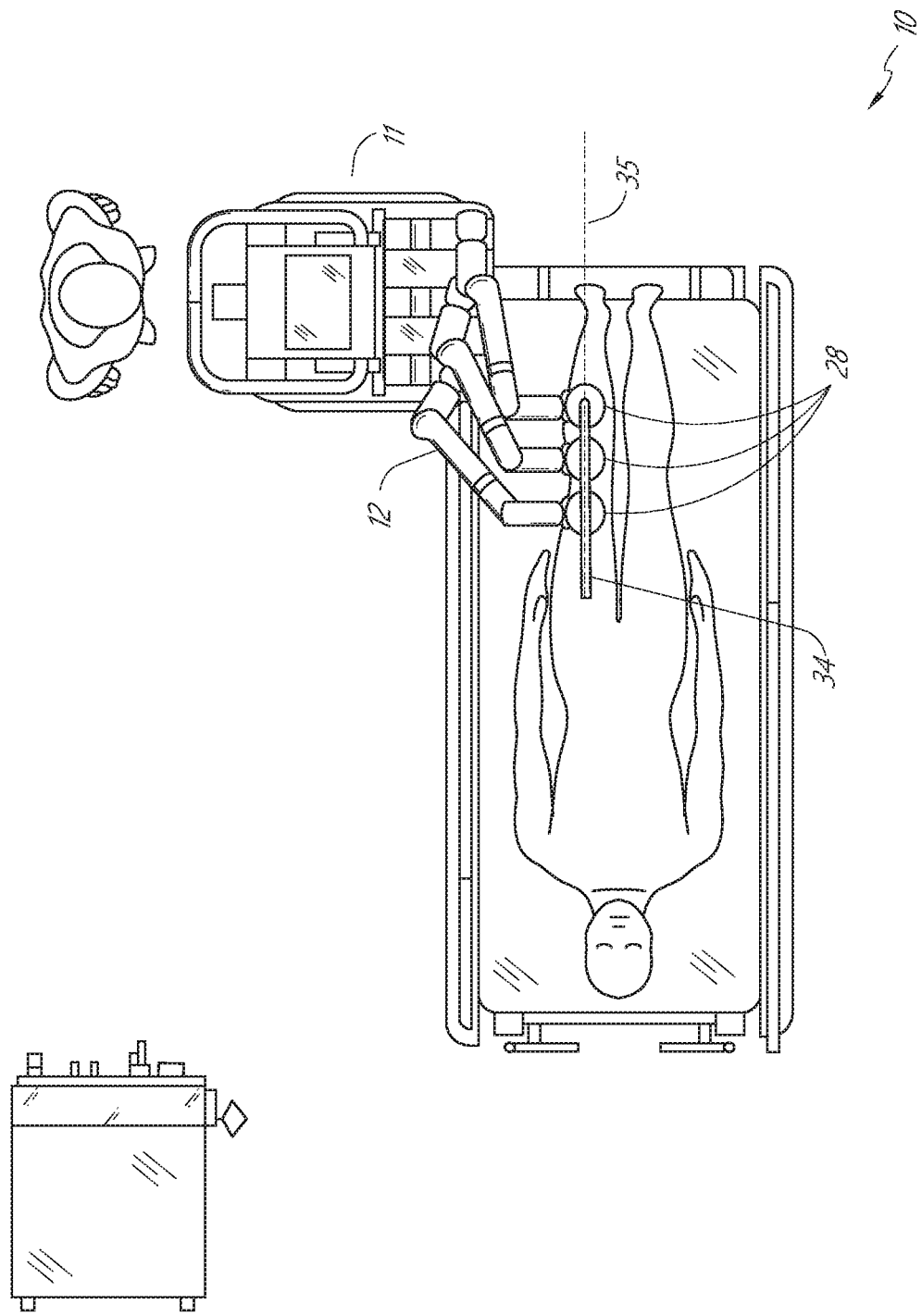
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
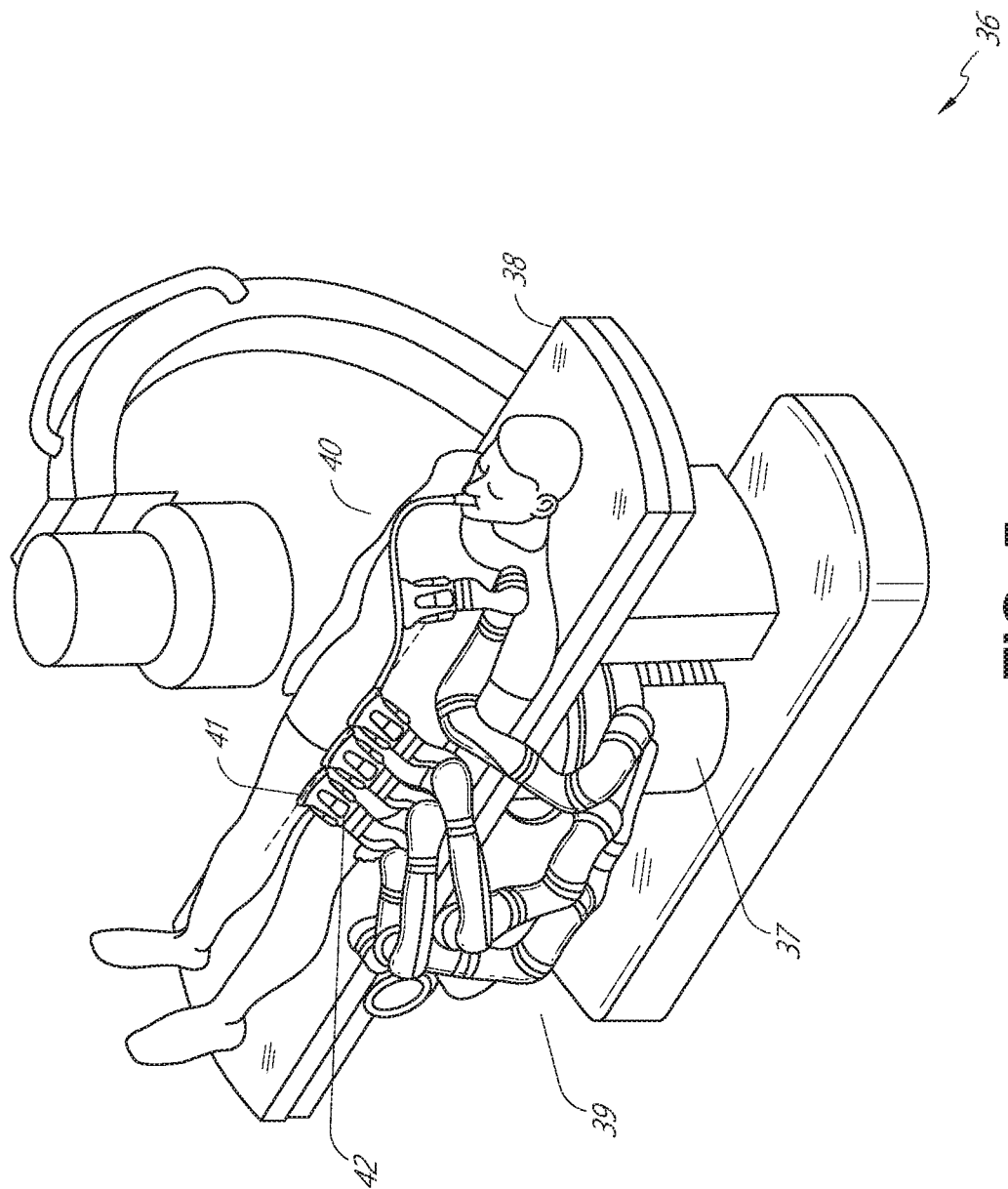
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
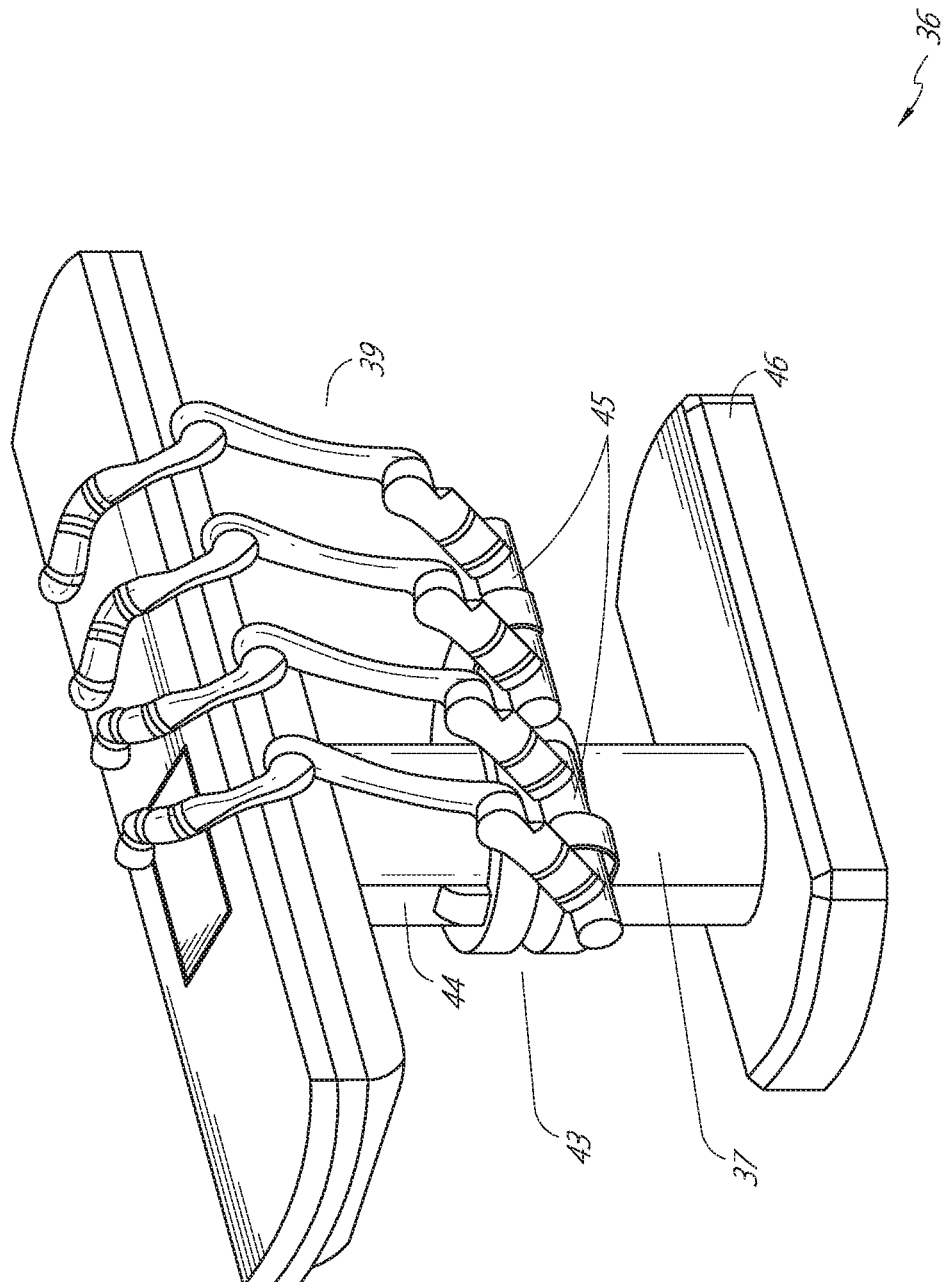
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
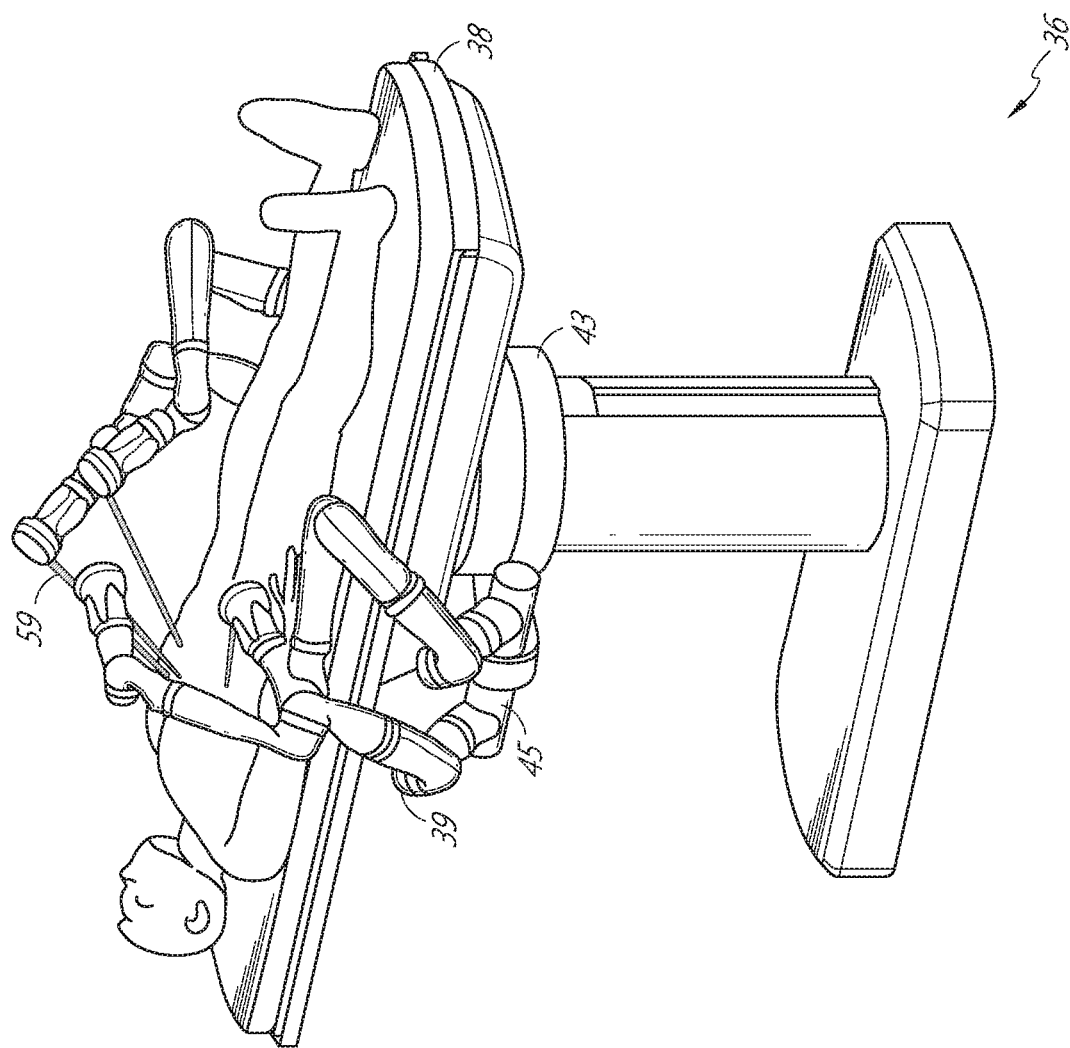
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
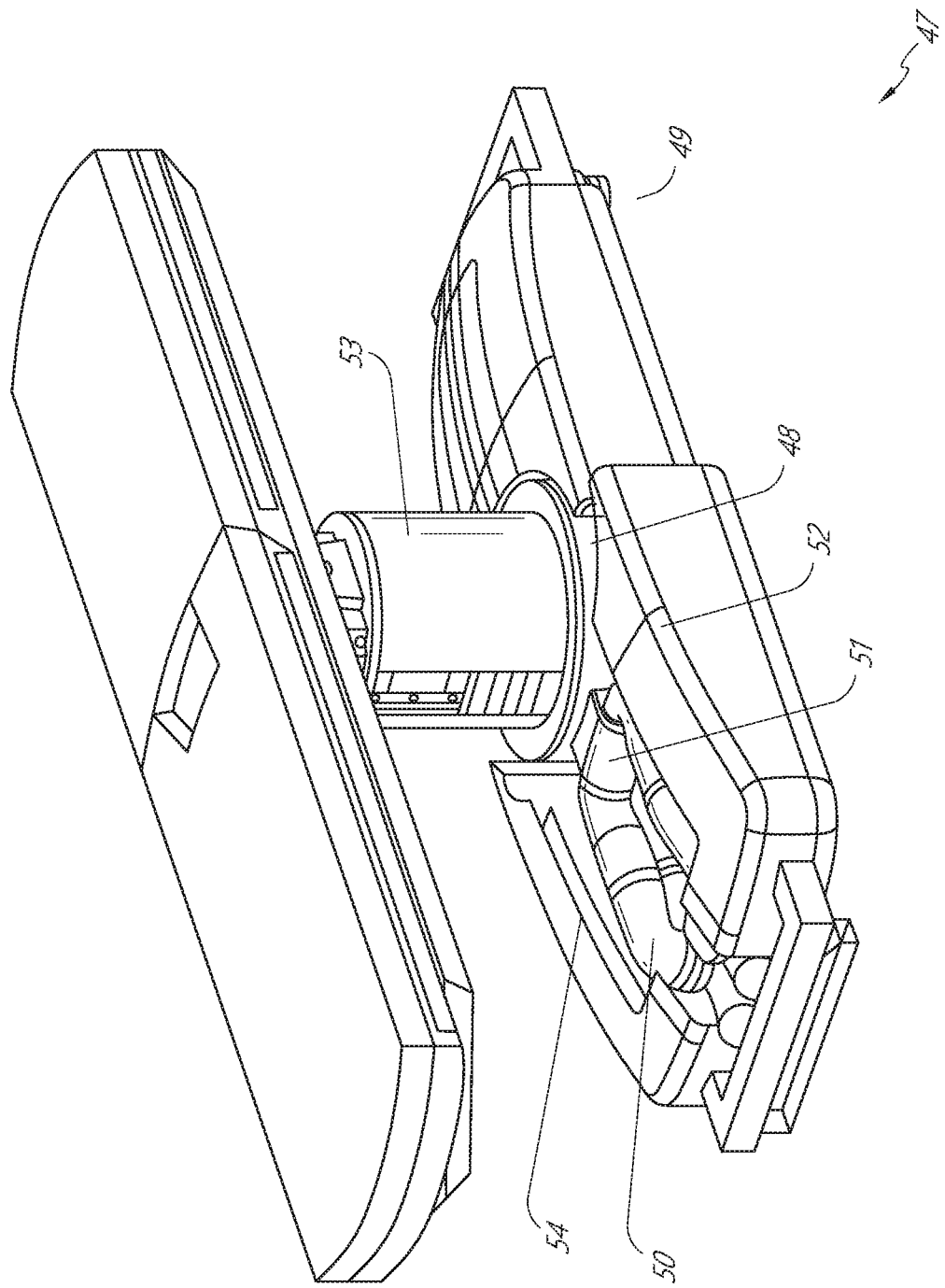
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
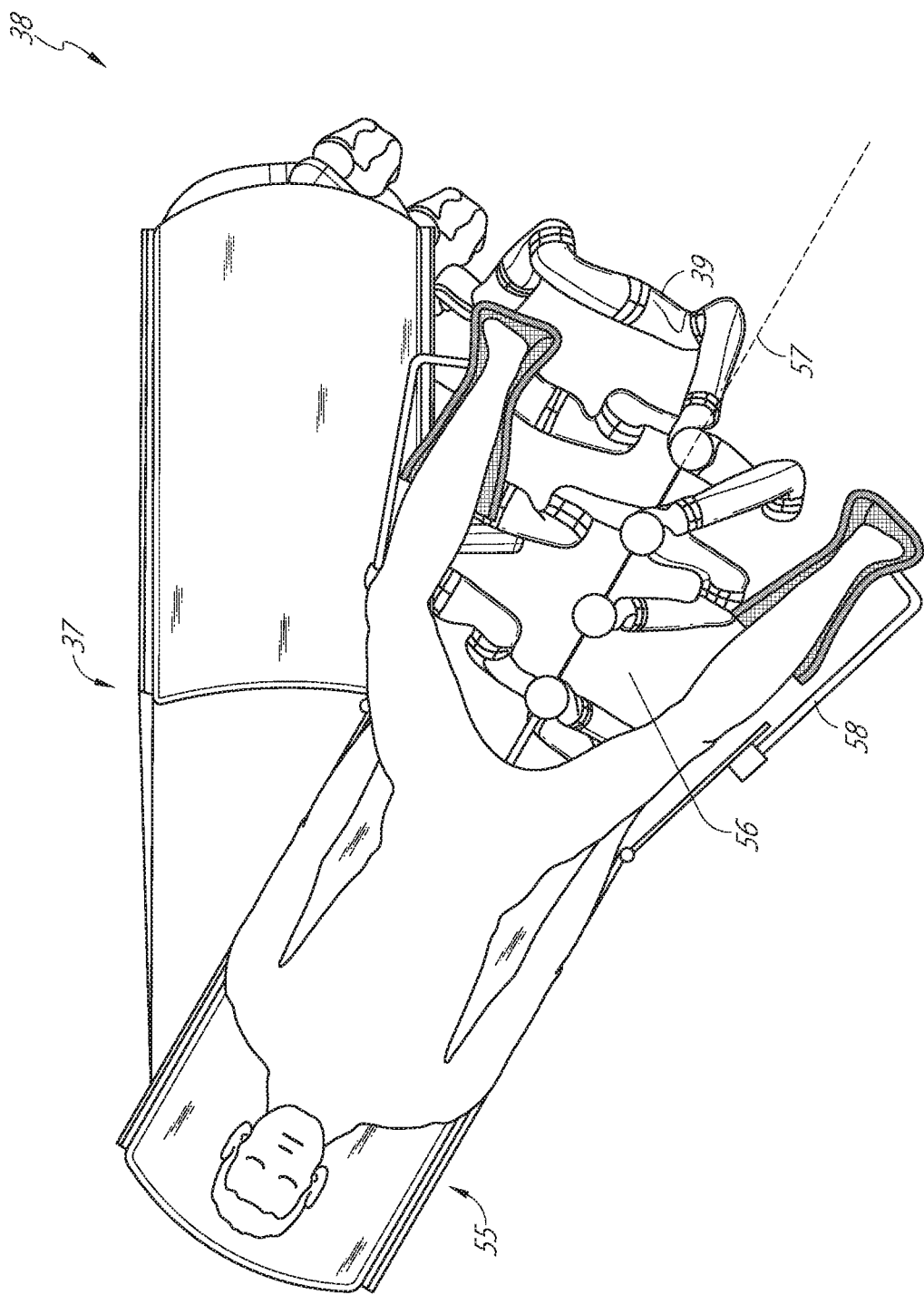
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
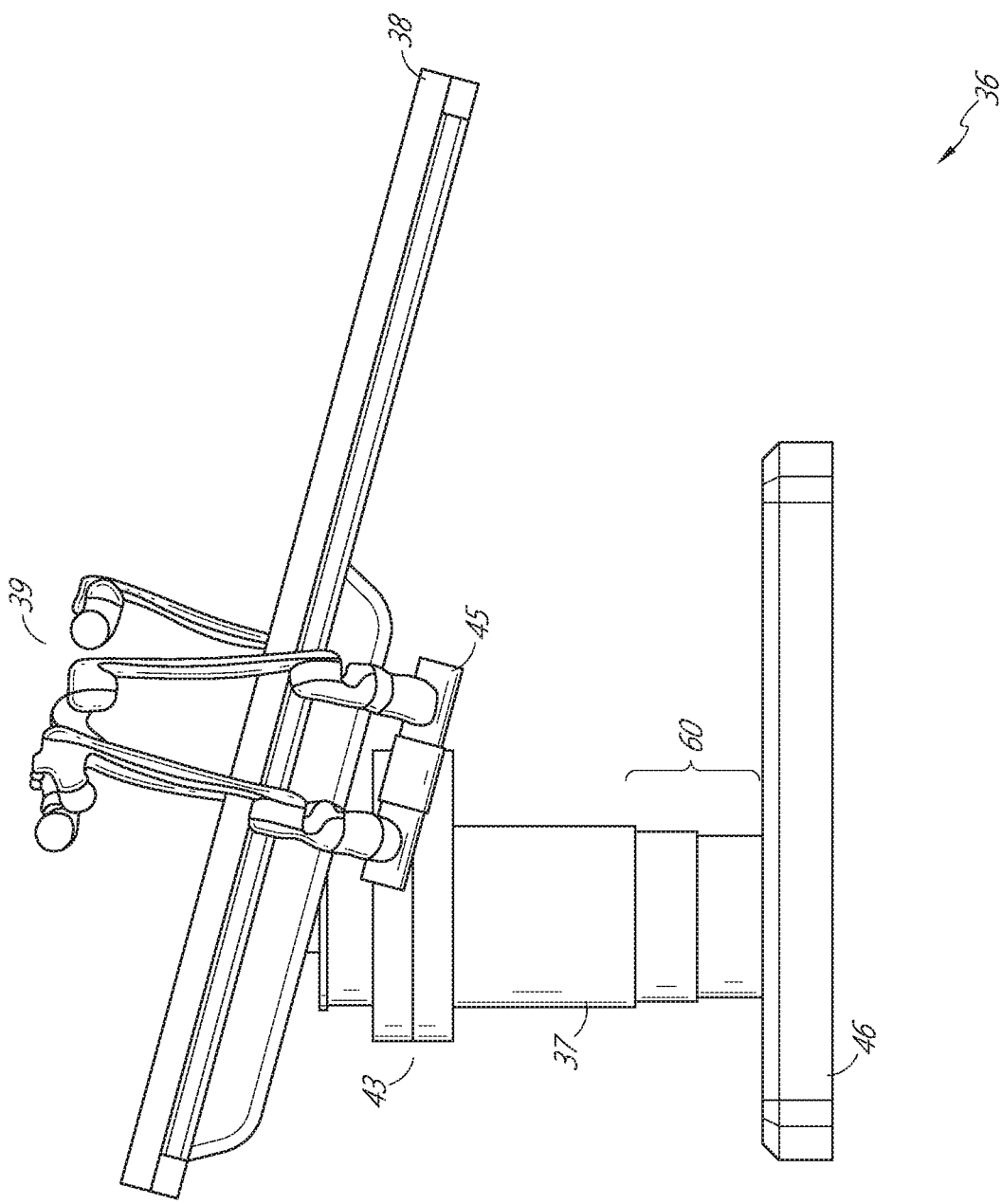
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
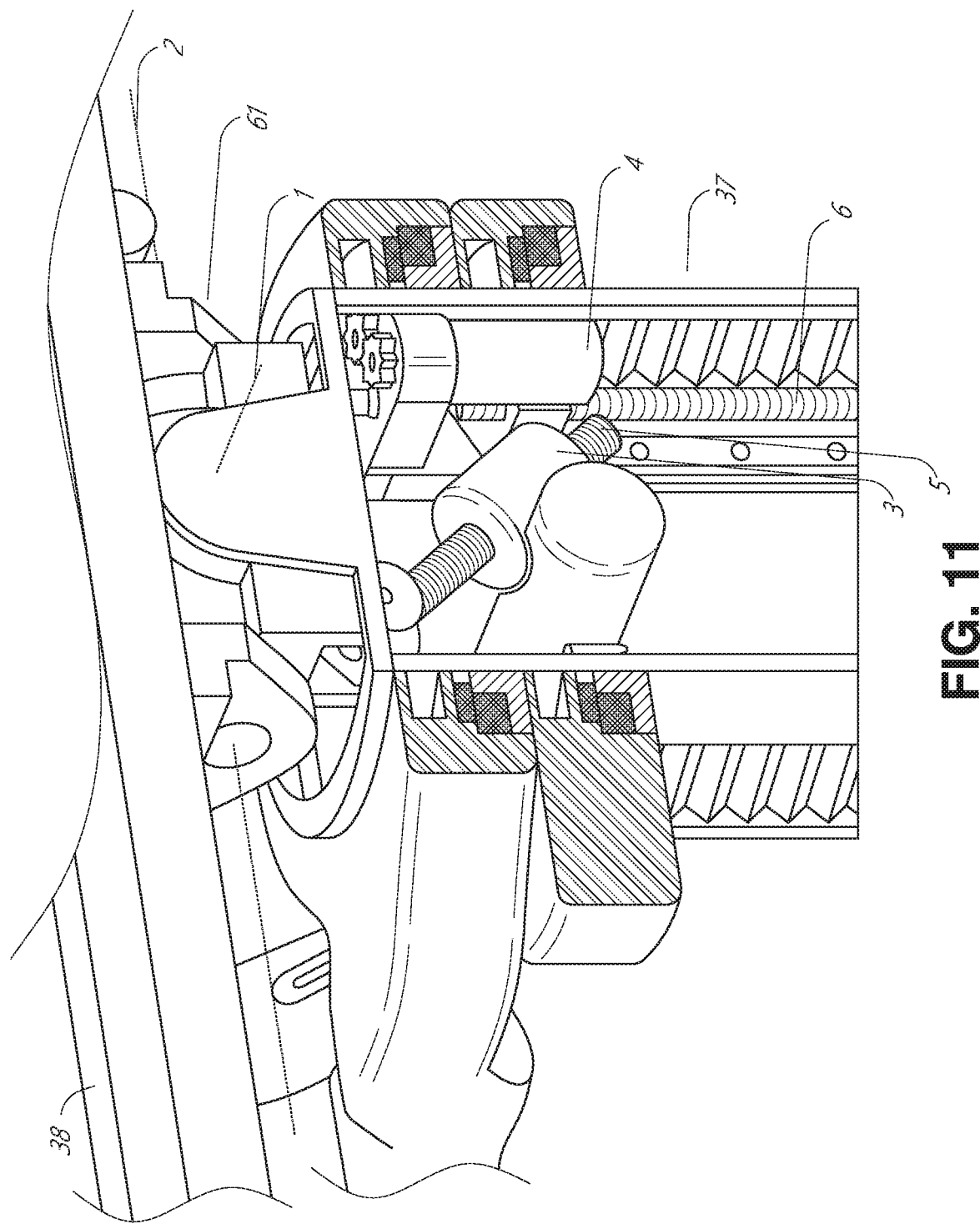
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
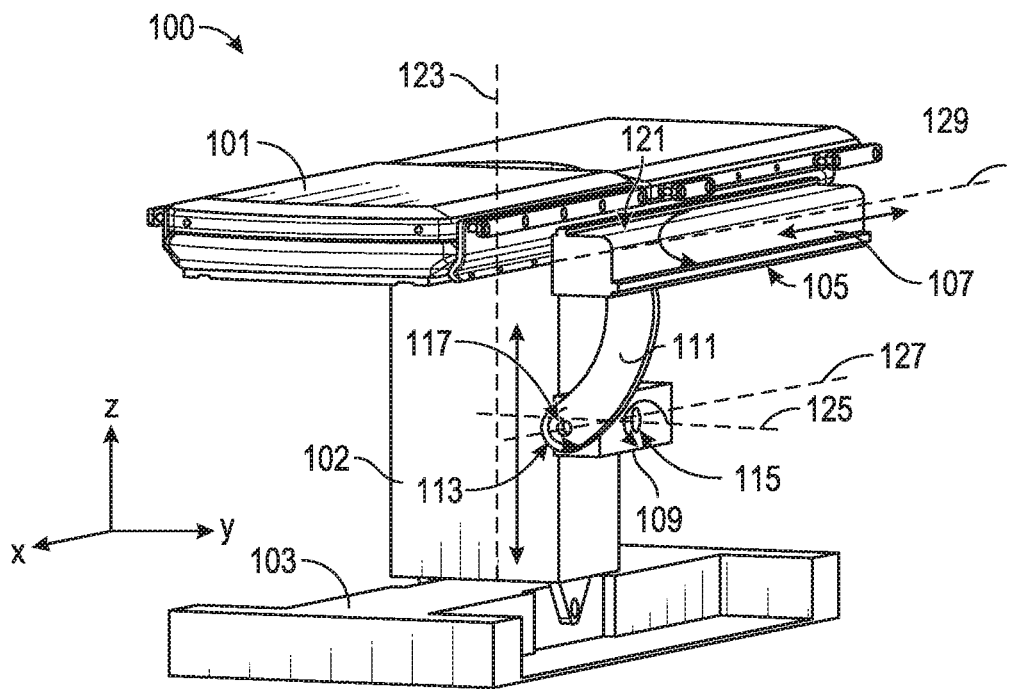
FIG. 12 illustrates an alternative embodiment of a table-based robotic system.
Figure 13:
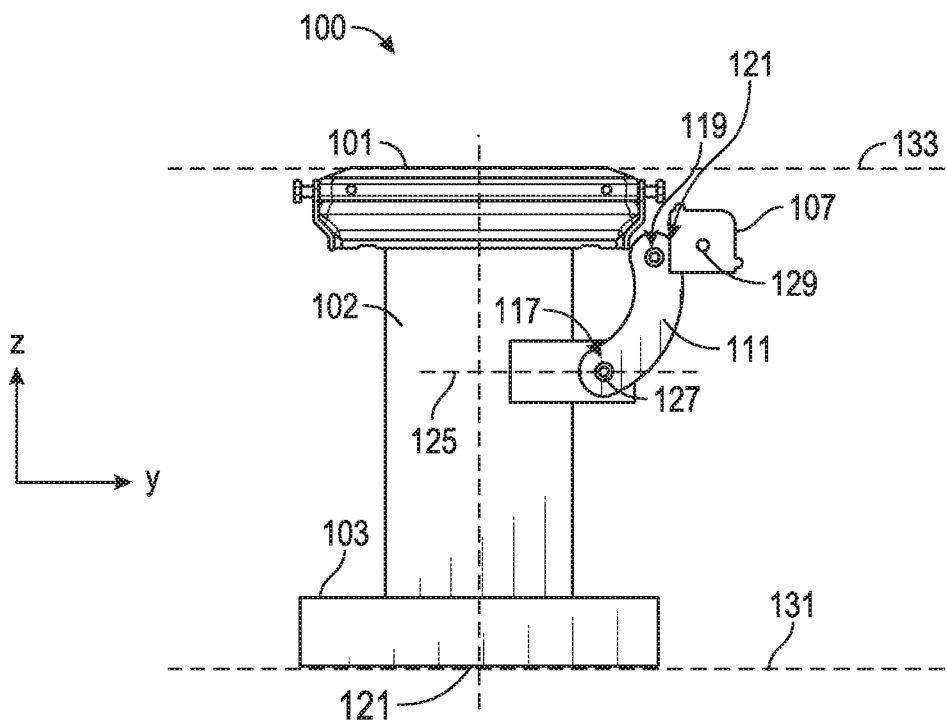
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support 105 can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
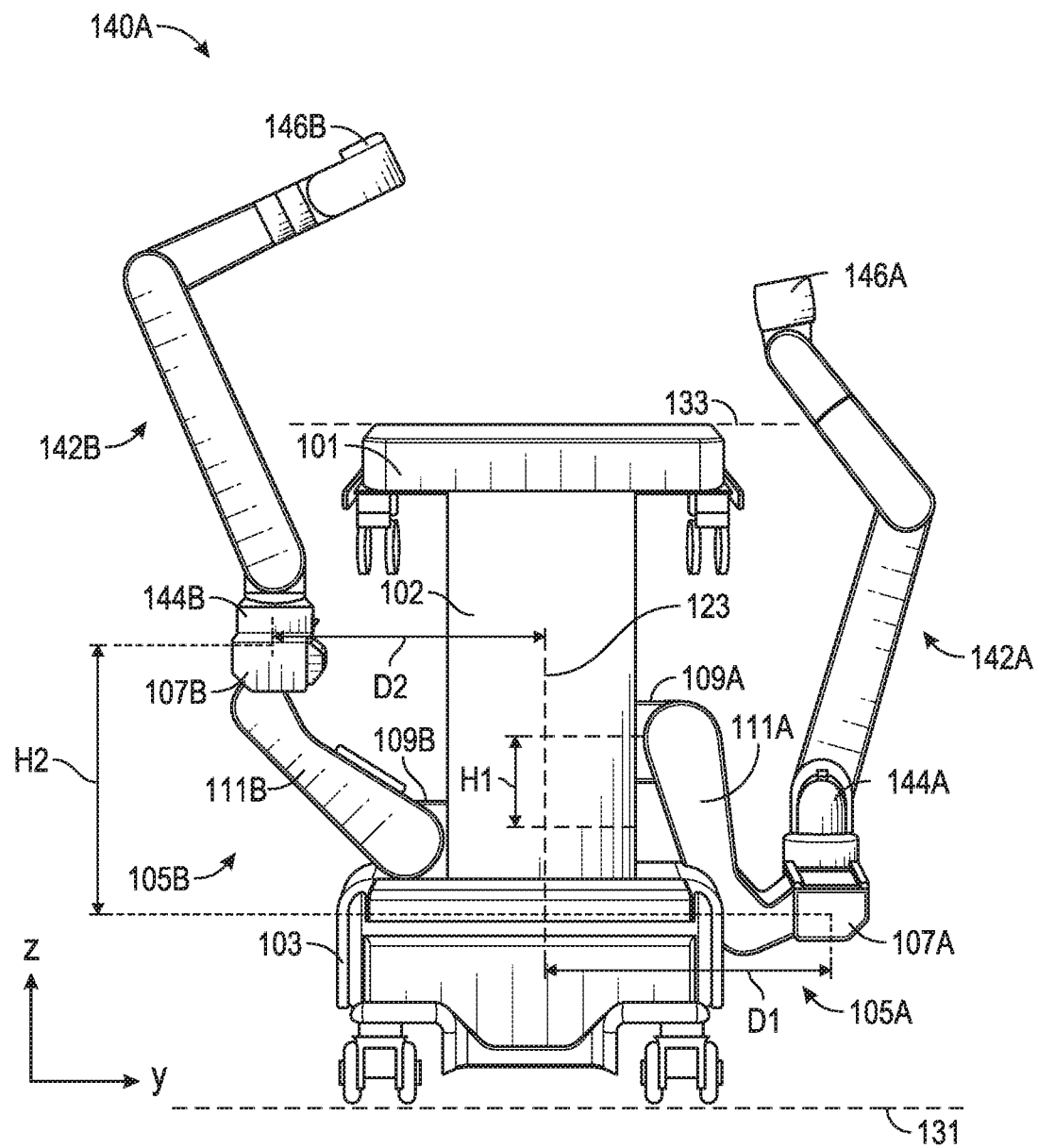
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
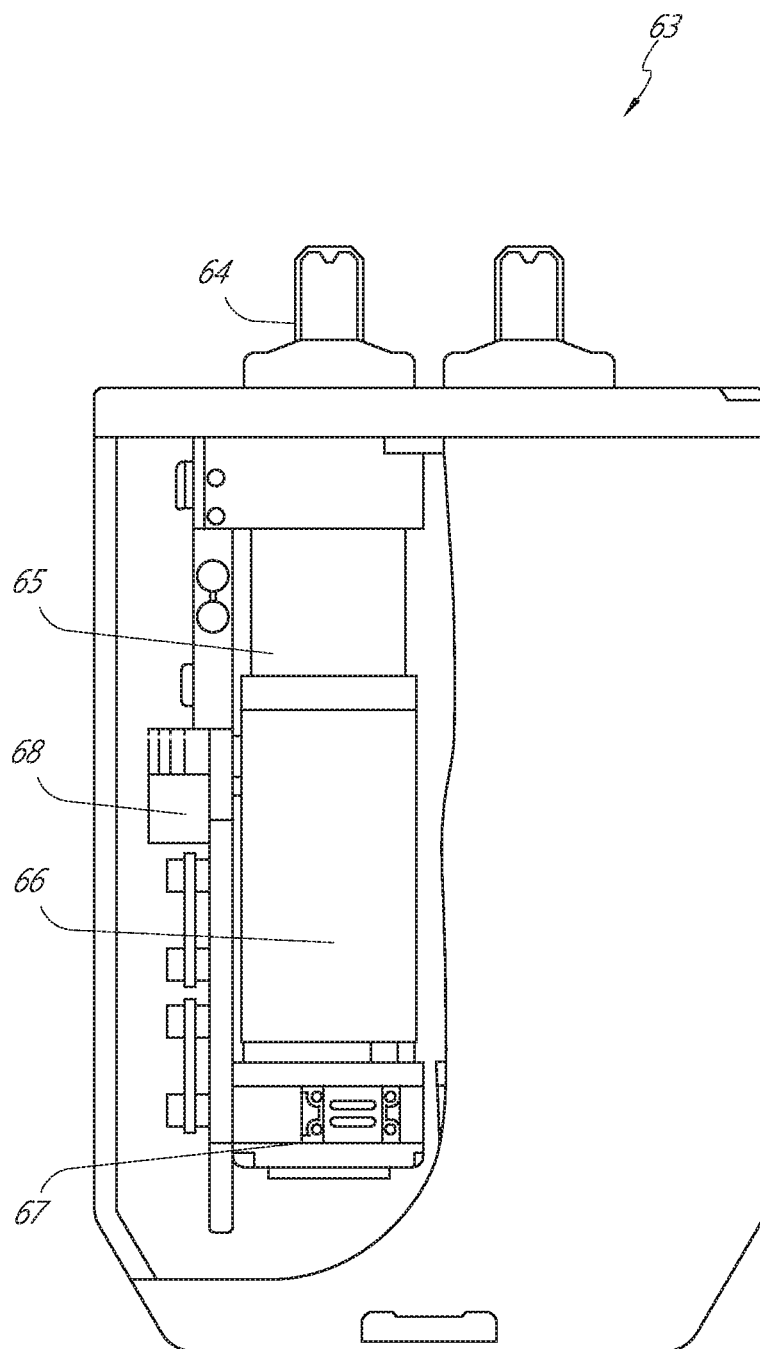
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
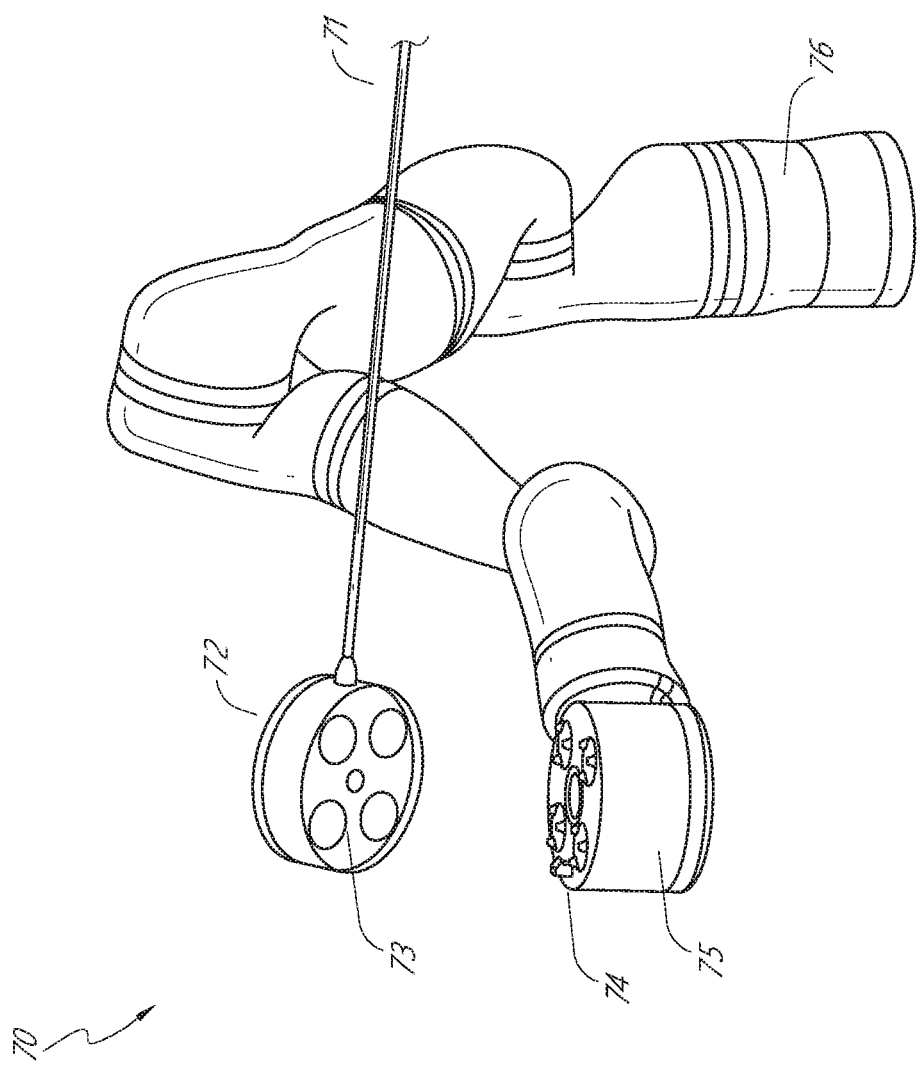
FIG. 16 illustrates an exemplary medical instrument with a paired instrument driver.

FIG. 16 illustrates an example medical instrument with a paired instrument driver Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the instrument handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
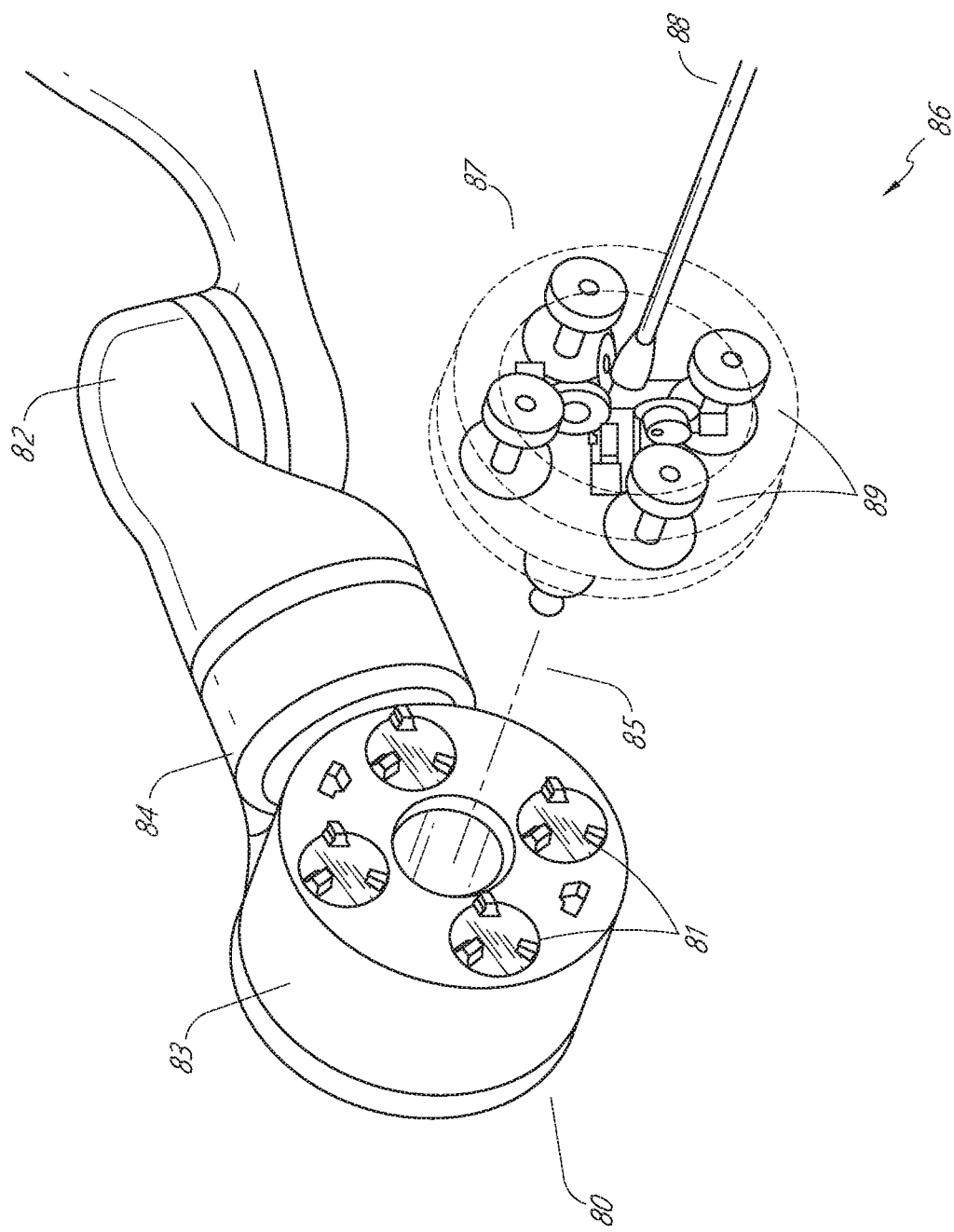
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
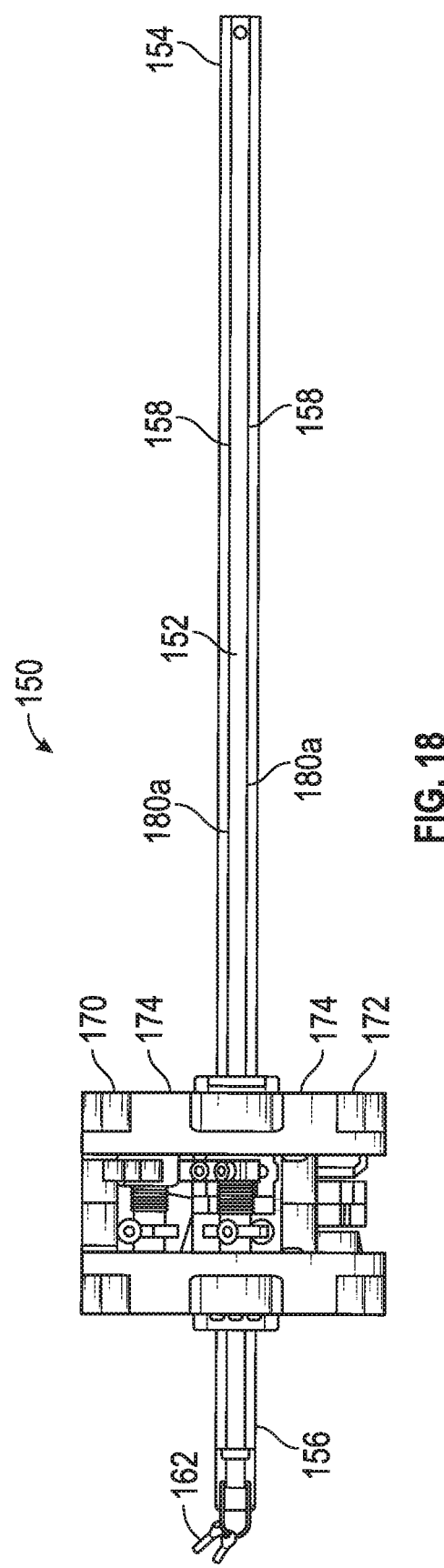
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver. In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
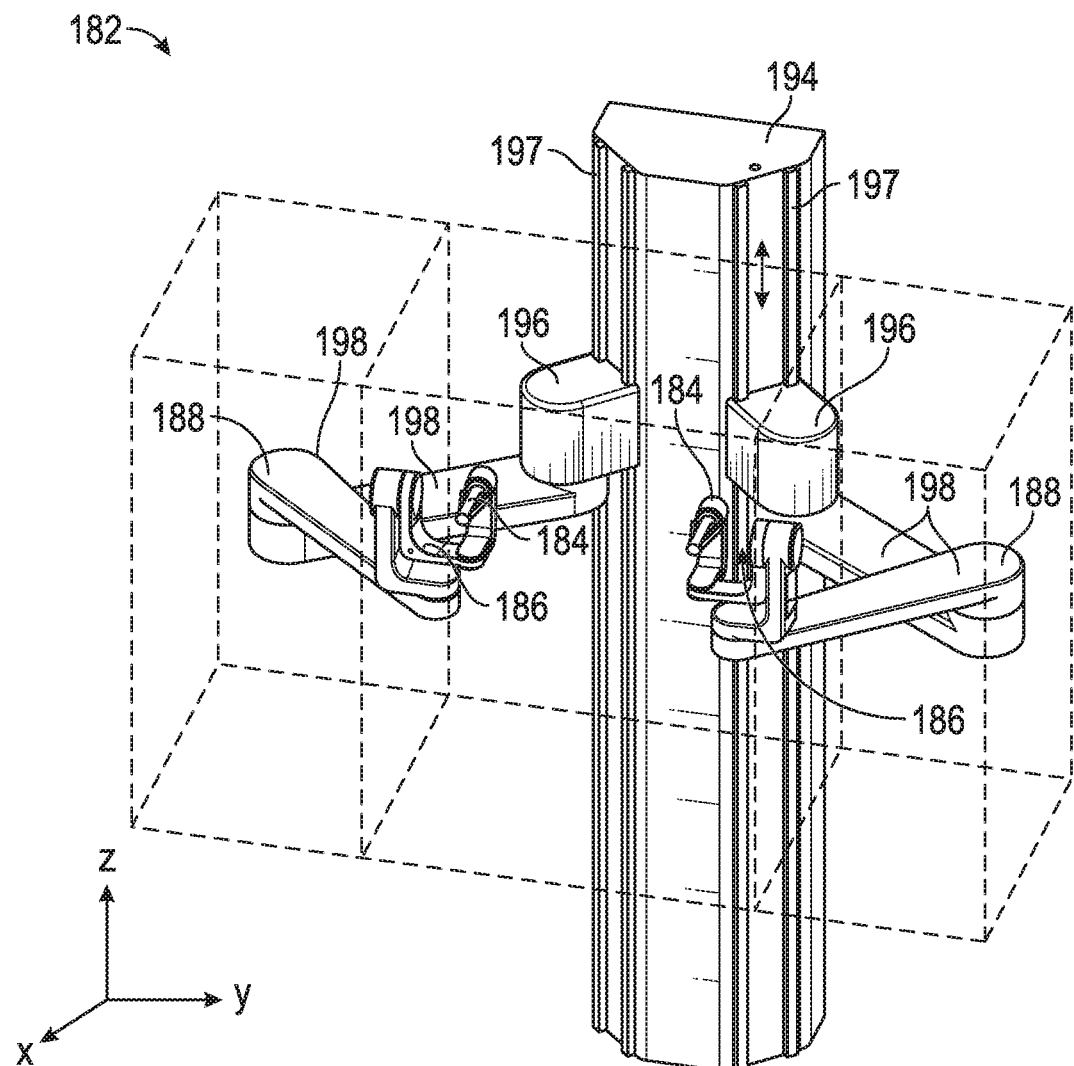
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188. Each gimbal can allow the user to manipulate the handle in the three orientation degrees of freedom (e.g., pitch, yaw, and roll).

As shown in FIG. 19, each positioning platform 188 includes a selective compliance assembly robot arm (SCARA) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA 198 is configured to allow motion of the handle 184 in an x-y plane, providing two additional degrees of freedom.

Figure 20:
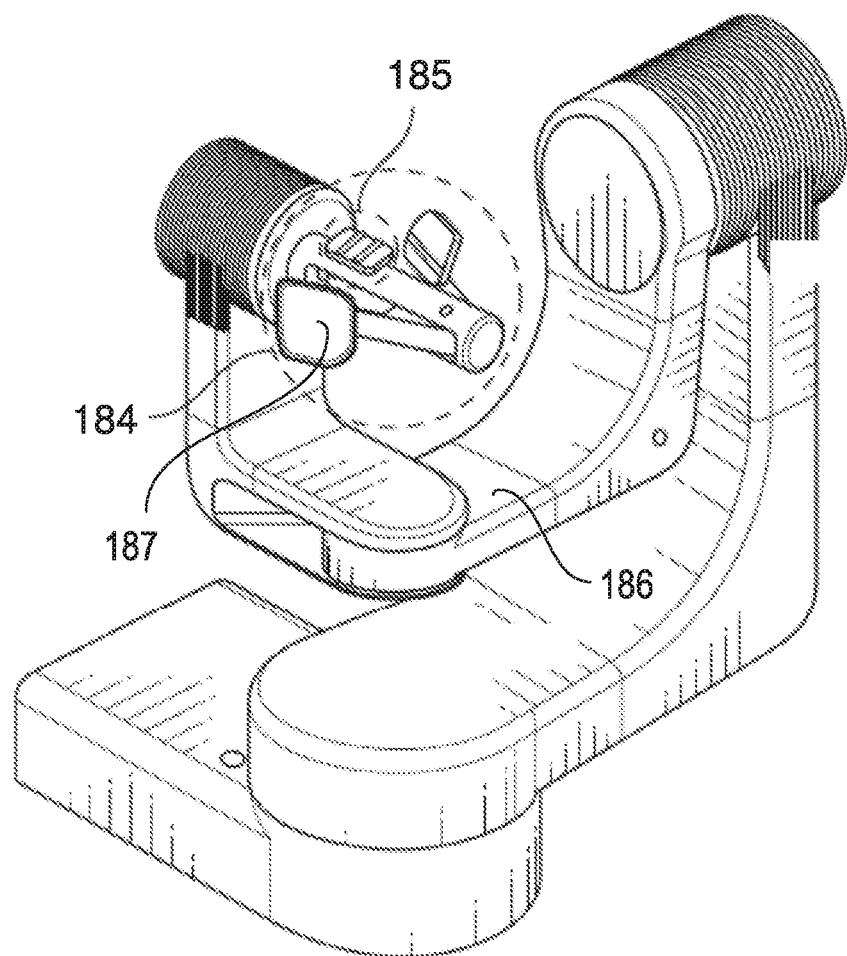
FIG. 20 illustrates a close-up view of an aspect of a handle that can be used with any console aspects disclosed herein.

FIG. 20 illustrates a close-up view of an aspect of a handle 184 that can be used with any console aspects disclosed herein. The aspect of the handle 184 shown in FIG. 20 can be used in any systems or methods disclosed herein, and can have any additional or alternative features or components including or in the alternative to those disclosed herein. Handle 184 can be used for either the first (which can be the left) handle or the second (which can be the right) handle. The handle 184 can optionally include a button 185 and finger-grips 187. The button 185 can provide a user input which allows the user to actuate features of the robotic system, including but not limited to an end effector of the corresponding medical instrument. The finger-grips 187 can provide an input which can allow the user to grab the handle 184 and manipulate the position of the handle 184 in six degrees of freedom.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 21:
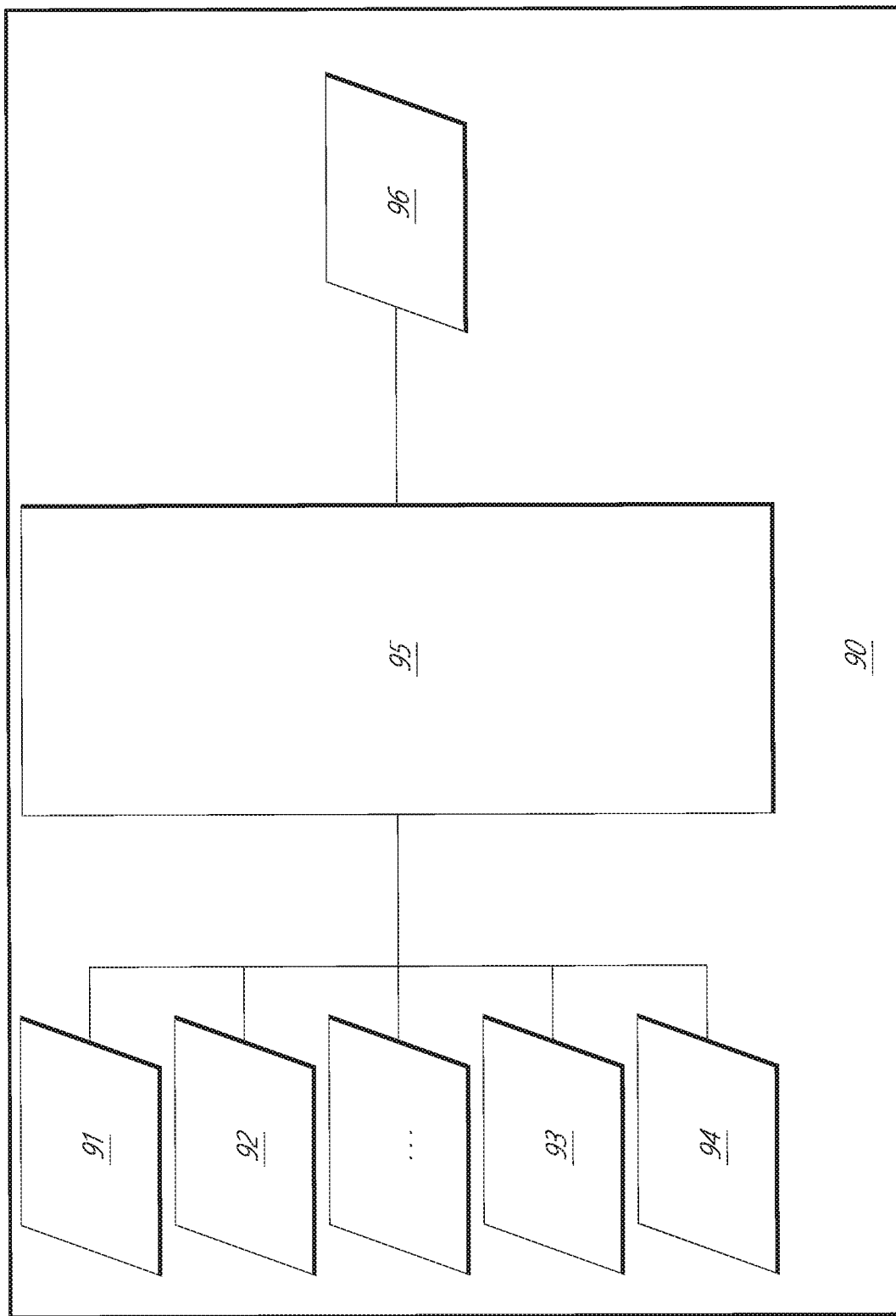
FIG. 21 depicts a block diagram illustrating a localization system that estimates a location of one or more elements of the robotic systems of FIGS. 1-10, such as the location of the instrument of FIGS. 16-18, in accordance to an example embodiment.

FIG. 21 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 21, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be used by the localization module 95 to generate model data 91. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92 to the localization module 95. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking and EM data 93 to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide location data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 21 shows, a number of other input data can be used by the localization module 95. For example, although not shown in FIG. 21, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Overlays and Controls in Physician Console Viewer

Any of the aspects of the console overlay and control system disclosed herein can be used with or integrated into any suitable robotically-enabled medical system capable of performing medical procedures, including without limitation both minimally invasive and non-invasive procedures, such as but not limited to open surgery, laparoscopy, endoscopy, combined endoscopic and laparoscopic surgeries (CELS) and other procedures. The aspects of the console overlay and control system disclosed herein can be used with a robotically-enabled medical system that can be configured in a variety of ways depending on the particular procedure(s) to be performed.

The console overlay and control system aspects disclosed herein can benefit the surgeon by permitting the surgeon to perform a greater range of tasks without requiring the surgeon to remove his or her attention from the viewer (which can be communicatively coupled with an imaging device such as a laparoscope or other scope or optical device and configured to render one or more digital images based on image data from the imaging device), enabling the surgeon to perform a variety of different procedures more efficiently and with a greater level of safety for the patient. For example, the surgeon can perform more procedures without requiring the surgeon to view a secondary screen or display, such as a touch screen, secondary monitor, or, in some aspects or procedures, without requiring the surgeon to view the operating bed or other components of the robotic system to perform particular operations or procedures, as will be discussed. In some embodiments, aspects of the console overlay and control systems disclosed herein can be configured such that the additional procedures that are herein enabled to be performed using the viewer can be performed without requiring the surgeon to perform any complex or difficult gestures or movements with the existing control hardware, thereby maintaining a simplistic control system and set of control procedures for the surgeon.

Any aspects of the systems disclosed herein can be configured such that a single user can control each or all of the robotic arms during a procedure. In any implementations disclosed herein, the system can have 6 robotic arms, or from 1 to 8 robotic arms, or from 4 to 6 robotic arms. The use of the overlays and controls can be particular beneficial for systems with multiple robotic arms, as will be discussed below.

Figure 22:
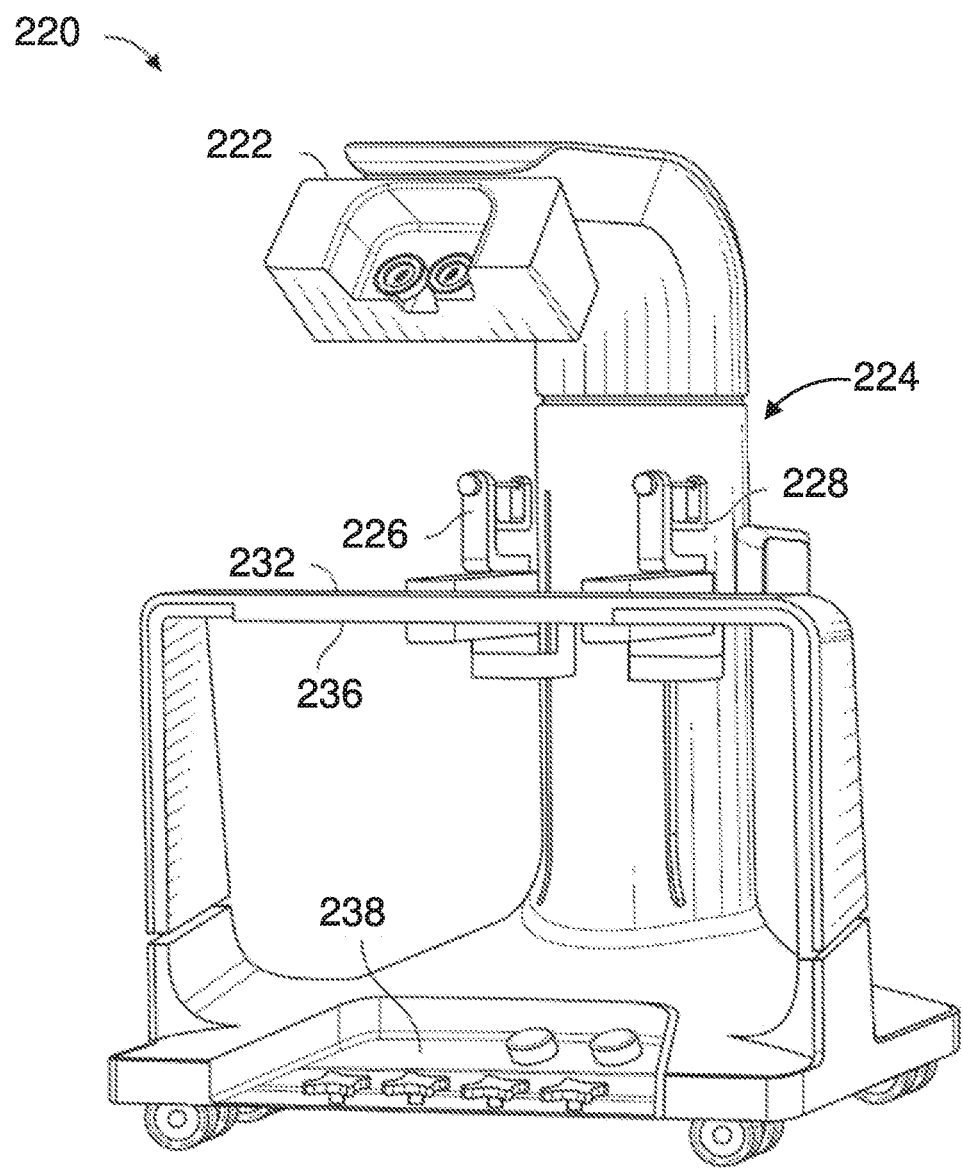
FIG. 22 is a perspective view of another example aspect of a console including one or more types of interfaces for controlling one or more robotic arms.
Figure 23:
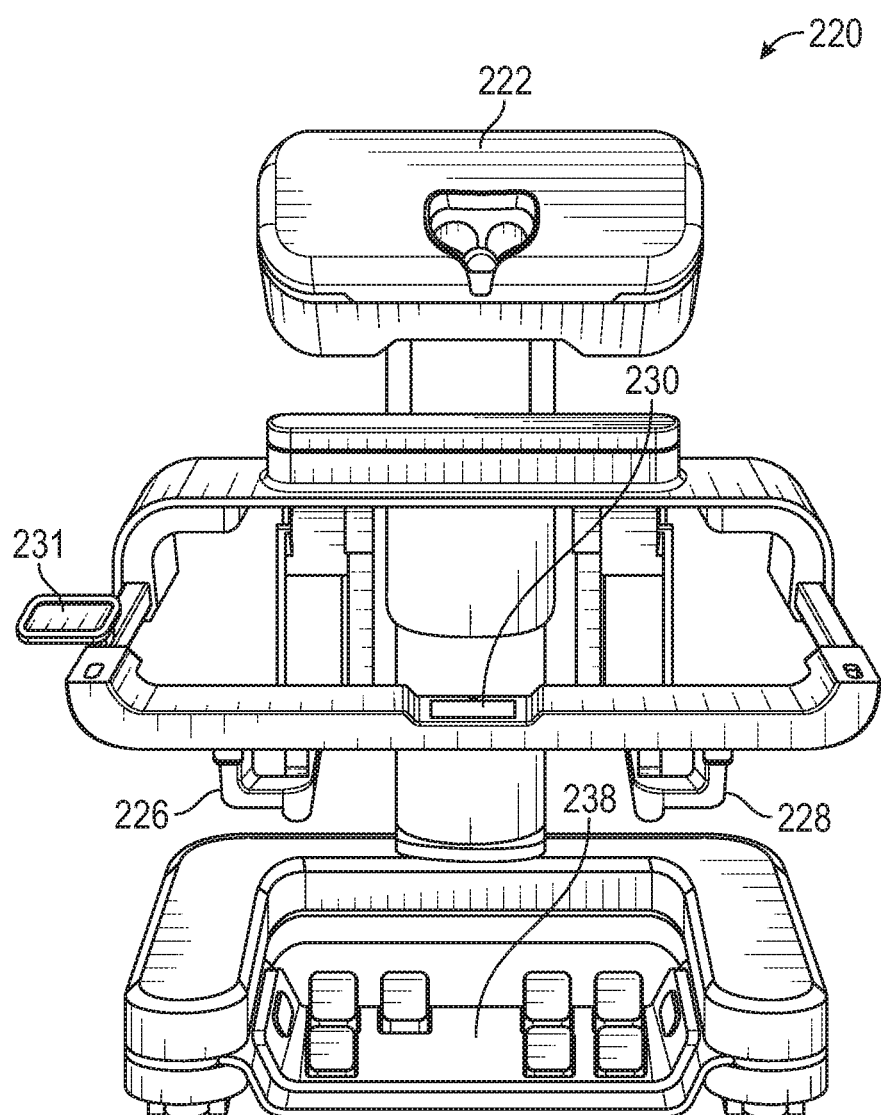
FIG. 23 is a front view of another example aspect of a console including one or more types of interfaces for controlling one or more robotic arms.
Figure 24:
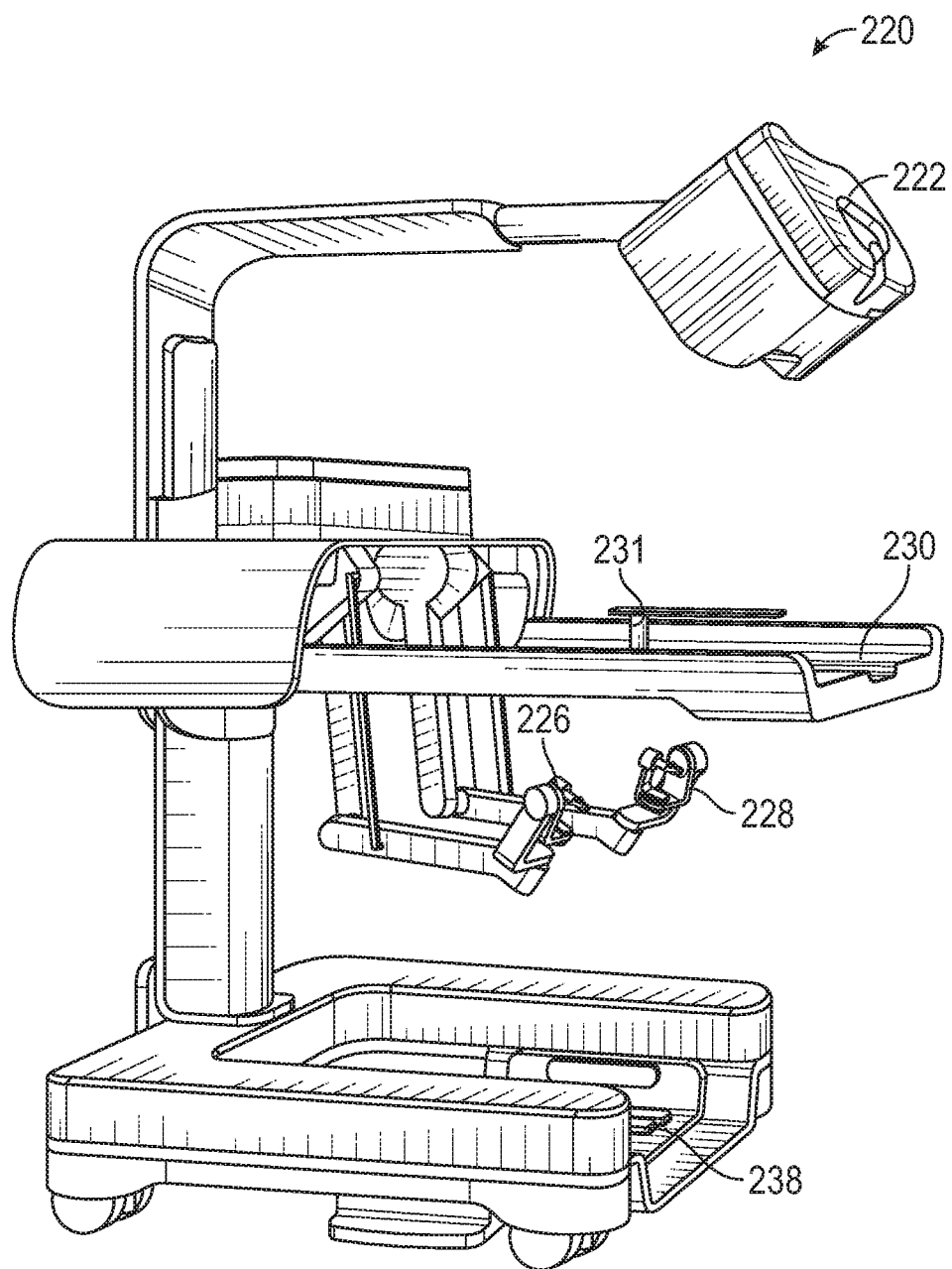
FIG. 24 is a side perspective view of the aspect of the console shown in FIG. 23.

FIG. 22 illustrates an example of a console 220 (also referred to herein as a physician console or a surgeon console) that can be used with any aspects of the surgical systems disclosed herein, including without limitation any of the systems described above, or any suitable table based or non-table based surgical systems currently being used or later developed. FIG. 23 is a front view of another example of a console 220 that can have any of the same features, components, and/or details of any of the other consoles disclosed herein, in addition to or in the alternative to any of the features shown in FIG. 23 and/or described herein. FIG. 24 is a side angle perspective view of the aspect of the console shown in FIG. 23.

In some embodiments, aspects of the physician console can include the following components: a viewer (e.g., without limitation, a stereoscopic viewer) that can allow a physician to see a surgical site piped in from an optical device/probe (e.g., a camera such as a laparoscope or endoscope) that is attached to one of the robotic arms, a master controller that can include a left handle 226 (which can be a gimbal type controller or other type of handle or controller), and a right handle 228 (which can be a gimbal type controller or other type of handle or controller). The left handle 226 can be configured to move one of the robotic arms and/or tools coupled thereto in response to a movement and/or other manipulation of the left handle 226. Similarly, the right handle 228 can be configured to move another one of the robotic arms and/or tools coupled thereto in response to a movement and/or other manipulation of the right handle 228. The physician console can also include one or more foot pedals, such as foot pedals 238. The foot pedals 238 can allow the user to perform different tasks, such as, e.g., switching control between different instruments, switching between instrument(s) and a camera, switching between the robotic arms, clutching (e.g., if a physician is in a non-ergonomic position and needs to move the arms comfortably, the clutch pedal can decouple the master controller from movement of the robotic arms while the physician gets into a comfortable position), actuating energy delivery devices, etc.

Any aspects of the console disclosed herein can optionally be cart based, as illustrated in FIGS. 22-24, or non-cart based, and can optionally include one or more types of interfaces and/or control mechanisms for controlling robotic arms in accordance with aspects of this disclosure. The console can include a viewer 222, a controller 224 including a pair of gimbals or handles 226, 228, configured to receive input from a user's left and right hands, as mentioned above. Any aspects of the console can also optionally include a pendant 232, an armrest 236, and/or one or more foot pedals 238. The first or left handle 184 can optionally be operated independently of the second or right handle 228. The console 220 can also include a touchscreen 230 that a surgeon can use to perform additional functions. Some aspects of the console 220 can also have a connection dock 231.

Figure 25:
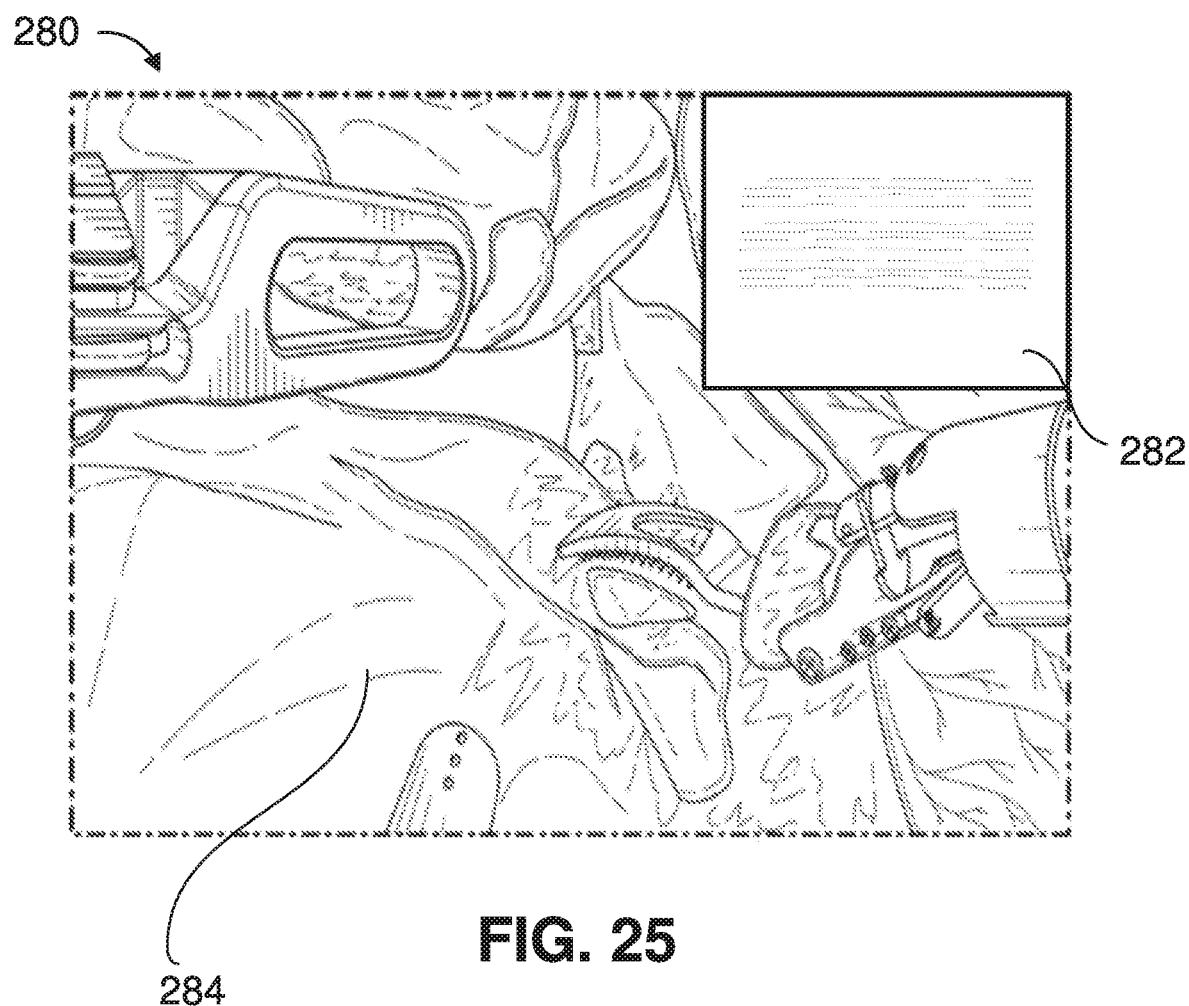
FIG. 25 is an example view which may be displayed by a viewer during medical procedures.

FIG. 25 is an example view 280 that can be displayed by a viewer of a physician console in accordance with aspects of this disclosure. In some aspects, the system may be configured to provide a computer-generated overlay of one image 282 on top of another image 284. Optionally, the computer-generated overlay 282 can be a visual rendering or graphical overlay of the position and orientation of the robotic arms, for example, as shown in FIG. 25. The non-interactive images 284 (as referred to herein as the base images) can include, without limitation, fluoroscopic images, endoscopic images, laparoscopic views and/or other images related to the patient, surgical site, or otherwise. In this configuration, the viewer can display two separate views in a view-on-view arrangement. In any aspects, the computer generated overlay 282 can be positioned in any desired position in the viewer, can have any desired size, and can optionally cover the entire base image 284.

Figure 27:
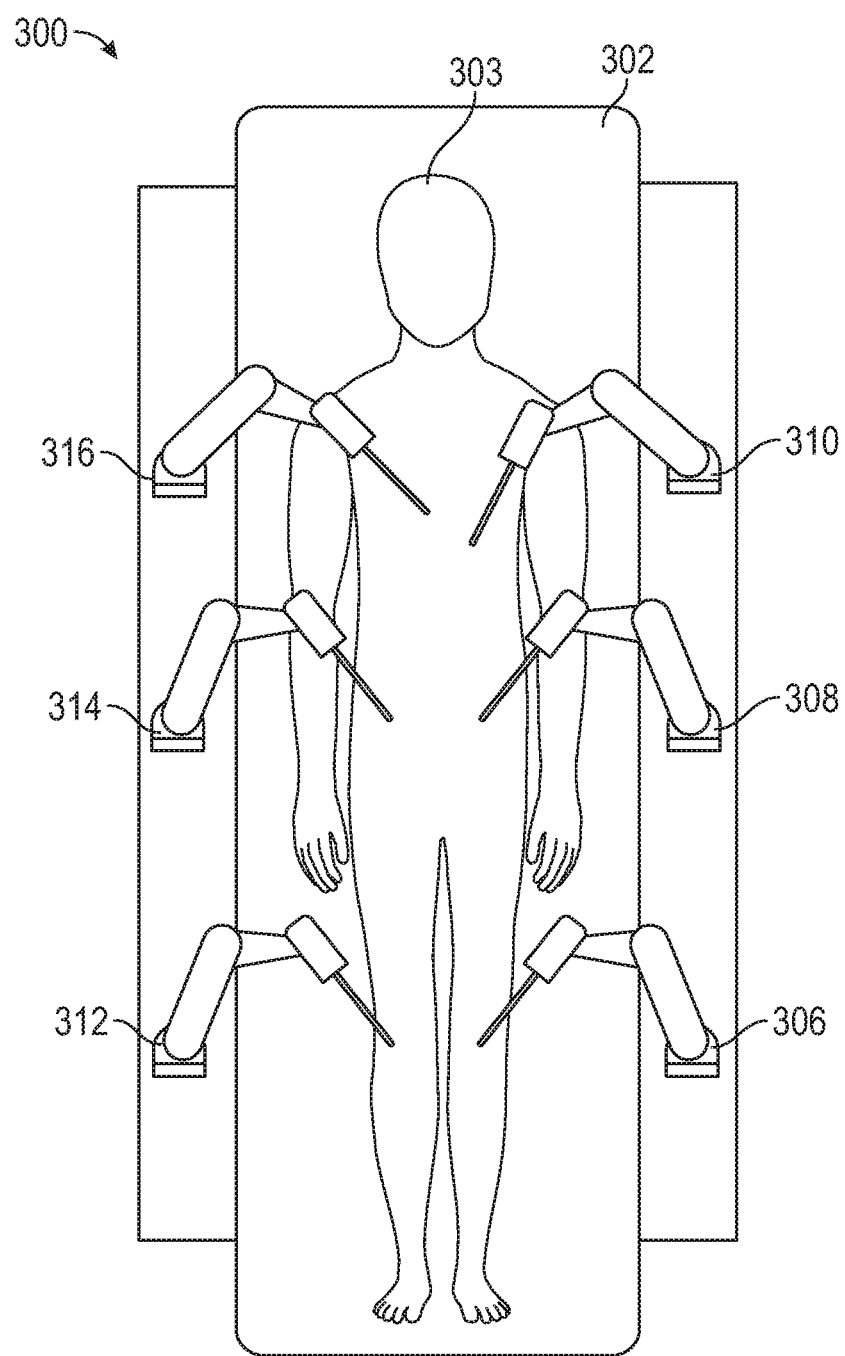
FIG. 27 shows a general representation of a visual rendering of a system having a table with a patient thereon and the robotic arms that are currently included in the system.

Any of the implementations disclosed herein can have an enhanced console and/or viewer, that can have any of the components, devices, features, or other details of any of the other console or viewer aspects disclosed herein, in addition to or in the alternative to any of the details disclosed below. In some aspects, the computer-generated overlay 282 (which can cover all or a portion of the non-interactive image 284) can comprise an interactive menu. Some aspects of the interactive menu can provide an "enhanced overlay" that can be overlayed on top of non-interactive images, as will be described in greater detail below. In some embodiments, the computer generated overlay 282 can include a visual rendering 300 that can be interacted with, as shown in FIG. 27. In other embodiments, the computer generated overlay 282 can include a menu that displays different available options for a surgeon during a surgical procedure.

Any aspects of the interactive menu and/or graphical renderings disclosed herein can optionally and advantageously be controlled using the same controls that the surgeon uses for performing the surgical operations and procedures, for example the handles and/or the foot pedals. In some aspects, additional control handles, knobs, buttons, dials, switches, joysticks, touch screen enabled devices, and/or any combination of the foregoing can be used to receive a user input for navigating the interactive menu, manipulating the interactive menu, and/or inputting information into the system related to the interactive menu.

By providing an enhanced overlay, which can comprise a graphical rendering of the position and orientation of the robotic arms, an interactive menu, etc., over the base image 284 within the viewer, the surgeon is able to observe the position and orientation of the robotic arms, instruments, and/or patient, or perform operations using the interactive menu, without removing his or her view from the viewer. These aspects can advantageously allow a physician to perform numerous functions (e.g., initiating instrument exchange between robotics arms) while keeping the physician's head and focus within the viewer, as opposed to contemporary systems, which require a surgeon to remove his or her eyes from the viewer and to view a separate viewer, such as a touchscreen device, to perform many of the operations and procedures that are capable of being performed using the enhanced viewer aspects of this disclosure. This can minimize the amount of down time during the procedure, and can minimize the disruptions during the surgical procedures to the entire surgical team.

The configuration of the viewer and/or interactive menu as disclosed herein therefore enables a much greater level of functionality to be performed by the surgeon without requiring the surgeon to remove his or her vision from the viewer, which has many safety and efficiency advantages. The interactive menu(s) and enhanced viewer disclosed herein can have the advantage of and can be configured to remove the need for a surgeon to remove his head from the viewer and reduce the number of interruptions to the surgeon or surgical team during a surgical procedure.

As discussed, any aspects of the systems disclosed herein can have any or any combination of the following components: a viewer, a touch screen, a connection dock, foot pedals, and a master controller. The viewer can optionally be a stereoscopic viewer, which shows the surgical site as viewed by a camera (e.g., a laparoscope). The touch screen can be used in addition to the viewer and can be configured to provide an additional input mechanism for the surgeon, or interaction with the surgeon. The system can optionally be configured such that any interactive menu or graphical representation that is transmitted into the stereoscopic viewer can also be provided on the touch screen, and vice versa. As mentioned, the console can also include an electrical connection dock. The connection dock can be coupled to a smartphone, mobile device, or other personal electronic device that can transmit information into the console.

In any implementations disclosed herein, the console overlay and control system can be configured to be selectively changeable from a first state, in which the master controller (such as master controller 182 shown in FIG. 19 or master controller 224 shown in FIG. 22) can be used to control one or more robotic arms or instruments, to a second state, in which the master controller can be used to manipulate the interactive menu and/or graphical renderings. Changing from the first state to the second state can be based on a user input into the system. Optionally, the system can be configured such that, in the second state, the robotic arms and/or instruments coupled therewith can be locked or frozen in their current position, despite any movement of the master controller (which can include a first and a second handle, which can be gimbals). In the second state, a movement of the master controller can cause a movement of a pointer on the interactive menu or other manipulation of the interactive menu, a manipulation of the visual rendering, or other interaction with the overlay, without resulting in any movement of the one or more robotic arms, instruments coupled therewith, or camera, thereby eliminating any inadvertent movements of the robotic arms and/or instruments coupled therewith.

In some aspects, the enhanced overlay can be displayed over a non-interactive graphical representation or image, such as overlay 282 (depicted schematically) in FIG. 25. In some aspects, the enhanced overlay can be displayed completely over a live or still feed or a graphical representation, while in other aspects, the enhanced overlay can be displayed so to be partially over a live or still feed or the graphical representation.

Aspects of the console overlay and control system disclosed herein can include at least one computer-readable memory device having stored thereon executable instructions, and one or more processors in communication with the at least one computer-readable memory configured to execute the instructions. The one or more processors can cause the system to at least cause movement of one or more robotic arms based on a user input received at the master controller. This can optionally occur when the system is in a first mode of operation. The one or more processors can also cause the system to cause the viewer to bring up or display the interactive menu and the graphical overlay on the viewer when a second user input is received at the master controller (which, in any aspects disclosed herein, can be master controller 182 shown in FIG. 19 or master controller 224 shown in FIG. 22). The interactive menu and/or the graphical overlay can be displayed over all or part of the one or more digital images that can be transmitted from the imaging device and displayed on the viewer.

Described below are some example methods of accessing and/or causing the system to display the interactive menu and/or graphical overlay described above that can be used with any of the console overlay and control system aspects disclosed herein (i.e., below are nonlimiting examples of the user input, also referred to herein as the second user input, for causing the system to display the interactive menus and/or graphical overlays in the viewer). In a first aspect, the console overlay and control system can be configured such that a substantially simultaneous actuation of a predetermined foot pedal or foot clutch pedal (such as foot pedal 238 of the console 220 shown in FIG. 22) and at least one of a first and a second finger clutch or button (such as button 185 of the console 220 shown in FIG. 22) can cause the system to display at least one of or, optionally, both of an enhanced overlay and an interactive menu in the viewer.

In another aspect, the console overlay and control system can be configured such that a substantially simultaneous actuation of a predetermined foot clutch pedal and both of the first and the second finger clutch can cause the system to display at least one of or, optionally, both of the enhanced overlay and the interactive menu in the viewer. The enhanced overlay can include information regarding the procedure that is being performed. Optionally, in some aspects, the system can be configured to cause the system to enter the second state when the interactive menus and/or graphical overlays is displayed, to eliminate inadvertent movement of the robotic arms. In any aspects, when the interactive menus and/or graphical overlays are displayed, the system can be configured such that any additional input received by the master controller can cause an interaction with the interactive menu(s) and/or graphical overlay(s), such as through a mouse type pointer or otherwise. Again, this can optionally occur when the system is in a second mode of operation.

In another aspect, the console overlay and control system can be configured to have a button, pedal, switch, or other input mechanism (hereinafter collectively referred to as the call up mechanism) for the purpose of displaying or actuating and/or removing or deactuating the interactive menus and/or graphical overlays in the viewer. Such call up mechanism can optionally include a foot pedal, a button on the console, a button or switch on the master controller (such as the first handle and/or the second handle), a depressible foot actuated track ball, or otherwise. Such call up mechanism can be located in the pedal bank, and can optionally be adjacent to the other foot pedals on the pedal bank. The system can optionally be configured such that the sole function of the call up mechanism is actuation and deactuation, manipulation of, and/or providing input to the interactive menus and/or graphical overlays.

In other aspects, actuation of the call up mechanism can be used for other functions or processes in the system, or be used for other purposes in the alternative to actuation and/or deactuation of the interactive menus and/or graphical overlays or in addition to this function. In some aspects, the call up mechanism can be triggered by the physician when the physician desires to call up menu functionality (which can include one or more graphical overlays) while their head remains in the viewer. Once a menu is brought up by the physician, the handles (for example, the handles 226, 228 of the console 220 shown in FIG. 22) and/or other components of the master controller can be used to manipulate the interactive menus and/or graphical overlays such that the master controller can be used as a virtual mouse, but optionally not used to manipulate or move the one or more robotic arms. In any aspects, the handles can operate like a computer mouse to move a cursor or pointer, make selections on the interactive menus and/or graphical overlays, drag and drop components of the interactive menus and/or graphical overlays, and/or perform other functions similar to the types of functions that can be performed using a computer mouse. Each handle of the master controller can optionally be used independently.

In another aspect, repetitive grip clicks of one or more of the handles (such as the handles 226, 228 of the console 220 shown in FIG. 22) can cause the system to display or hide the interactive menus and/or graphical overlays in the viewer. For example and without limitation, a double clicking input received by one or more of the handles 226, 228, or optionally a triple clicking input received by one or more of the handles 226, 228, or optionally a double clicking input received by both of the handles 226, 228 substantially simultaneously, or optionally double clicking in either of the handles 226, 228 while a predetermined foot pedal is depressed, can cause the system to display or hide the interactive menus and/or graphical overlays in the viewer.

In any implementations disclosed herein, the system can be configured such that, when the interactive menus and/or graphical overlays are deactuated or hidden from the viewer (which can, optionally, cause the system to change back to the first state), the handles 226, 228 can reorient themselves to the position and orientation that the handles 226, 228 were in at the moment that the user called up the interactive menus and/or graphical overlays. This can enable the surgeon to position his or her hands and arms in the same or similar position as they were when the surgeon was using the handle(s) 226, 228 to manipulate the robotic arm(s). In other words, the handles (which can, in any implementations disclosed herein, be gimbal type handles) can automatically reorient to the active instruments. The realignment of the handles can optionally be linked to the graphical visualization.

In other aspects, the system can be configured such that, a double clicking, simultaneous double clicking, triple clicking, double clicking while a foot pedal is depressed, or other similar user input could be used to change an instrument parameter like grip strength. For example, the system can be configured such that, if an instrument with variable grip strength has grip strength set too low, the physician can quickly double click the surgical master grip to increase grip strength by one unit. Optionally, double clicking again could cause the grip strength to increase by one more unit. A double click increase in grip strength would be shown on the screen to confirm the change. Similarly, a rapid triple-click could be used to turn grip strength down one unit, and be optionally repeated for additional adjustments. In alternative aspects, the click speed and number of clicks could be used to control different features like scaling, scope angle, or camera control.

Figure 26:
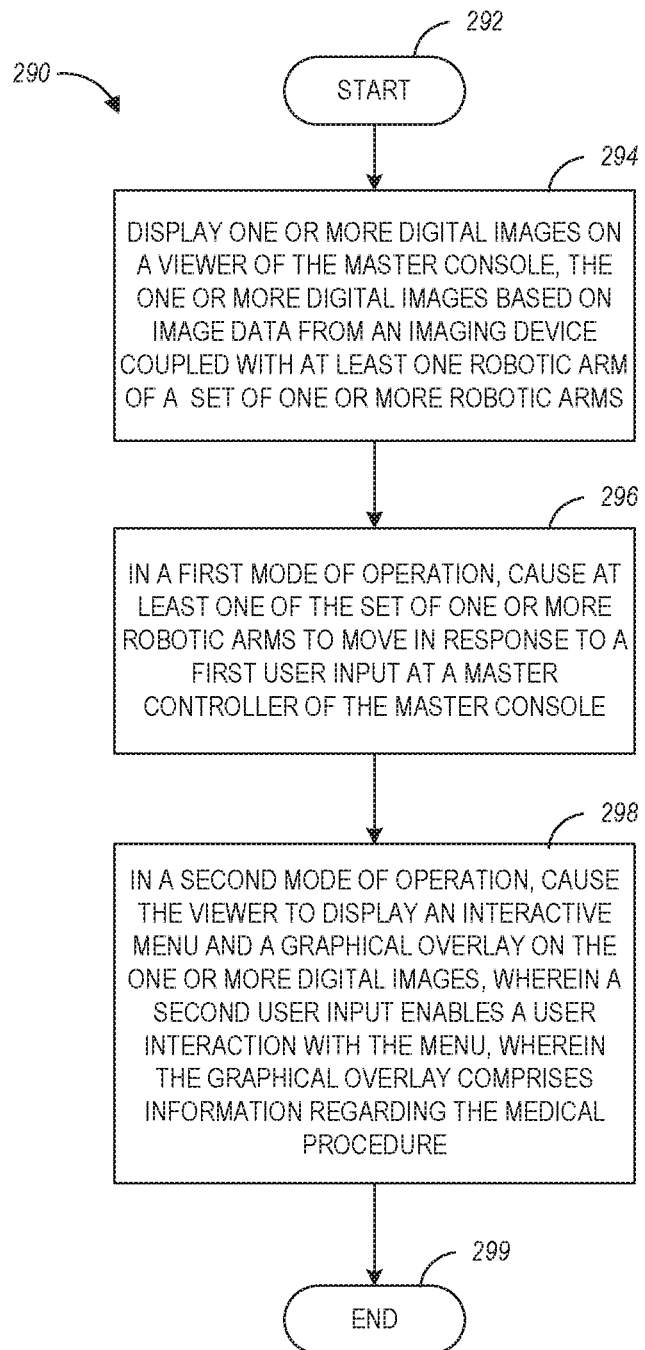
FIG. 26 depicts a flow chart of a method operable by a robotic system to display an interactive menu and allow a user to interact with the menu with a master controller.

FIG. 26 is a flowchart illustrating an example method operable by a robotic system, or component(s) thereof, in accordance with aspects of this disclosure. For example, the steps of method 290 illustrated in FIG. 26 may be performed by processor(s) and/or other component(s) of a robotic system, the system having a master console and a set of one or more robotic arms configured to perform a medical procedure.

The method 290 begins at block 292. At block 294, the system displays one or more digital images on a viewer of the master console, the one or more digital images based on image data from an imaging device coupled with at least one robotic arm of a set of one or more robotic arms.

At block 296, in a first mode of operation, the system causes at least one of the set of one or more robotic arms to move in response to a first user input at a master controller of the master console.

At block 298, in a second mode of operation, the system causes the viewer to display an interactive menu and a graphical overlay on the one or more digital images, wherein a second user input enables a user interaction with the menu, wherein the graphical overlay comprises information regarding the procedure. The method 290 ends at block 299.

A. System Visual Render.

As described above, implementations of the console overlay and control system can be configured to provide a visual rendering of the robotically-enabled medical system to inform the physician(s) of system, arm, and instrument status, in the viewer. Systems having four or more or six or more robotic arms can result in significant complexity and difficult to the surgeon manipulating the arms and instruments coupled therewith, maintaining desired orientation of the arms, and preventing undesirable interaction between the arms and instruments coupled therewith. For example, a system can be configured to have six robotic arms mounted bilaterally (three arms on each side of the patient). In this configuration, the visual rendering can provide the physician with an interactive graphical representation of arm position, patient position, instrument position, instrument trajectory, and/or instrument status. The visual rendering can also provide a visual representation of the orientation of the patient versus the table top (which can be input into the system or otherwise determined by the system).

When activated or called up, the interactive overlay that can include the visual rendering can at least partly cover the surgical view communicated to the viewer from a scope. A nonlimiting example of a visual rendering 300 is shown in FIG. 27, which shows a general representation of a visual rendering 300 of a system having a table 302 with a patient 303 thereon, and the robotic arms that are currently included in the system. In this aspect, the system may include a first robotic arm 306, a second robotic arm 308, and a third robotic arm 310 on one side of the table 302, as well as a fourth robotic arm 312, a fifth robotic arm 314, and a sixth robotic arm 316 on another side of the table 302. The visual rendering 300 can generally depict the exact and/or relative position and orientation of each of the robotic arms 306, 308, 310, 312, 314, and 316 with respect to both the patient 303 and table 302, and provide a quick visual summary to the user regarding which handle is currently assigned to each of the robotic arms. The visual rendering 300 can help the user perceive context and status of the system quickly and easily within the viewer (i.e., without having to remove his or her view from the viewer). In some embodiments, the visual rendering can be visually accurate and represent the many configurations of the bars, robotic arms, table, and/or patient. The visual rendering can provide a real-time visual representation of the system, with an update or visual refresh occurring at a predetermined interval. For example and without limitation, the visual rendering can provide an accurate visual representation of the system every 0.5 seconds, or from every 0.05 second or less to every 1 second or more, or from every 0.1 second to every 0.5 second, or from and to any value within these ranges. The system can also be configured to permit the user to activate a refresh of the visual rendering. Alternatively, the visual rendering can be a static or gross representation of the overall system status.

Additionally, any aspects of the system can be configured such that the visual rendering provides a three-dimensional representation of the system. The three-dimensional representation can optionally be configured such that a user can manipulate the three-dimensional visual rendering. For example and without limitation, the system can be configured such that the visual rendering can be rotated, panned, zoomed in or out, or otherwise changed in response to input received by the master controller. For example, without limitation, a user can pinch a first gimbal controller together, or can depress a first foot pedal, or perform some other movement or manipulation of the master controller, to zoom into or enlarge a portion of the visual rendering. A user can pinch in on a second gimbal controller, pinch out on the first gimbal controller, depress a second foot pedal, or perform some other movement or manipulation of the master controller to zoom out of the visual rendering. Rotating a gimbal controller can cause a rotation of the visual rendering.

B. Assigning of Handedness.

Figure 28:
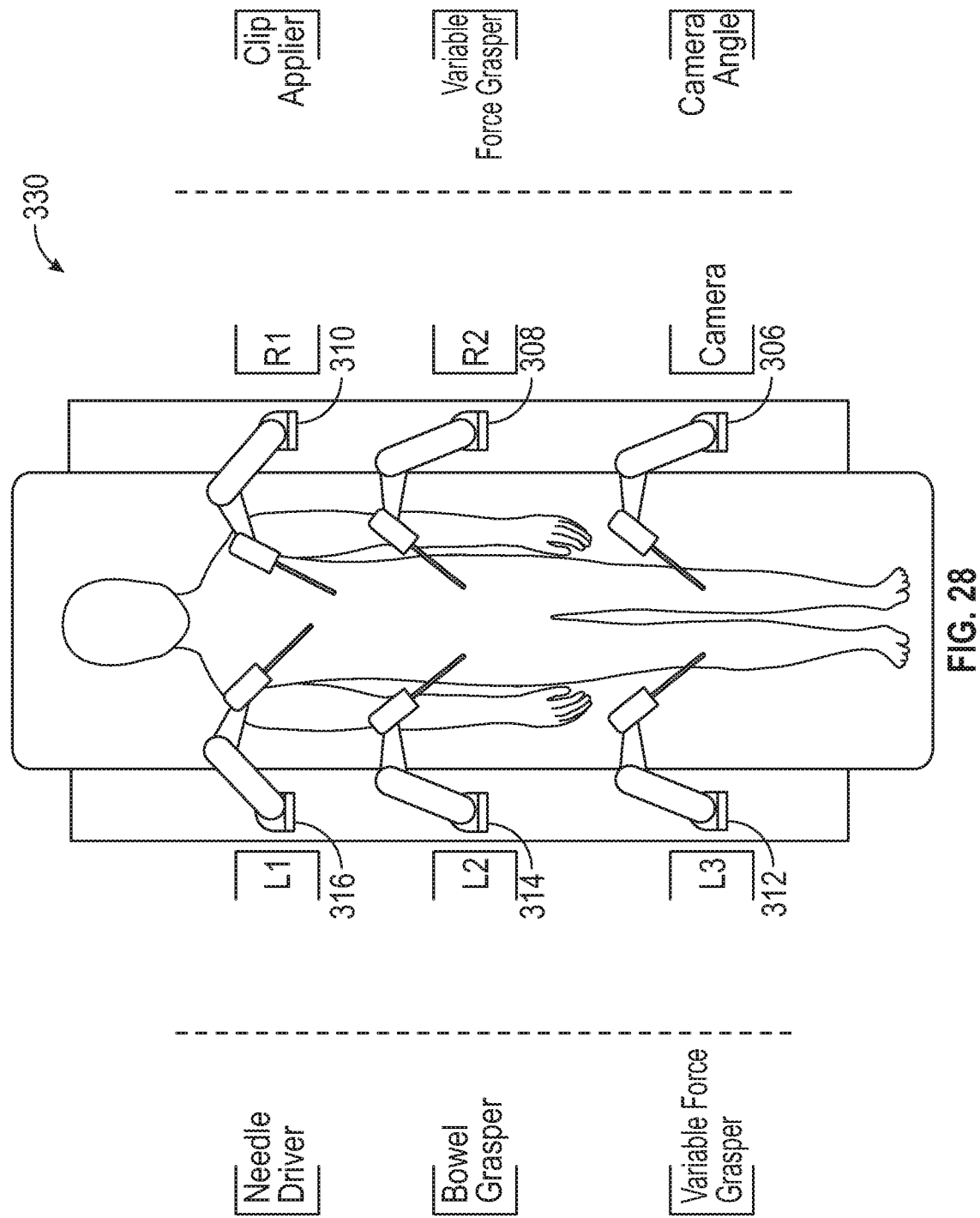
FIG. 28 illustrates an example of a graphical representation or handedness menu that can be displayed on the viewer.

Some aspects disclosed herein can be configured to enable a user to assign or change the handedness of the robotic arms, which refers to the assignment of left and right hand assignments to specific robotic arms of the system that have instruments installed on them by the physician, so that the physician can control whether the first or the second handle controls a particular instrument. FIG. 28 illustrates an example of graphical representation or handedness menu 330 that can be displayed on the viewer to inform the surgeon of the handedness assignment of the robotic arms and the particular instruments coupled therewith, and/or provides a menu with which the physician can change the handedness assignment of the particular robotic arms.

When the user commands or activates the handedness menu 330 to be displayed in the viewer, the handedness menu can be configured to cover all or part of the surgical field displayed on the viewer. The menu 330 can inform the user of which instrument is installed on or coupled with each respective arm, which robotic arm is currently being controlled by the first or left handle (which can be, e.g., a gimbal controller or the like), and which robotic arm is currently being controlled by the second or right handle (which can also be, e.g., a gimbal controller or the like). In some aspects, the menu 330 can also provide an accurate visual rendering of the position and/or orientation of the robotic arms 306-316 relative to the patient, as described above. For example, as shown in FIG. 28, one left arm (e.g., the sixth robotic arm 316) can be attached to a needle driver, while one right arm (e.g., the third robotic arm 310) can be attached to a clip applier.

The surgeon may utilize the menu 330 to assign/change the handedness assignments to each arm, meaning the surgeon would be able to change which arms are designated as being under left hand control and under right hand control. This interaction can optionally be done in a drag and drop fashion where both the left and right master handles (which can be gimbals) can serve similar functions to computer mice and their actuation can be used as a left click function that would allow the user to grab an item (e.g., L1) and drag and drop it to another location (for example, to move L1 from the sixth arm 316 to the third arm 310). This would mean that the left gimbal and the right gimbal would swap in terms of control of the instrument that was moved.

In any aspects, any of the inputs into the master controller described above (including the double clicking and triple clicking sequences described above) can be used to cause the system to pull up the interactive menu and/or graphical overlay that can be used to change the handedness associations of the various robotic arms.

C. Troubleshooting Arm Collisions.

Any implementations disclosed herein can also be configured to permit the surgeon to detect, troubleshoot, and avoid collisions of two or more robotic arms, nonrobotic arms, the patient, the table, and/or other objects. With existing systems, when physicians are operating with their heads in the viewer, there may not be a way for the physician to troubleshoot system collisions (e.g., arms colliding with one another, arms colliding with the bed, instrument shafts colliding with each other or with other arms) without removing his or her view from the viewer.

Figure 29:
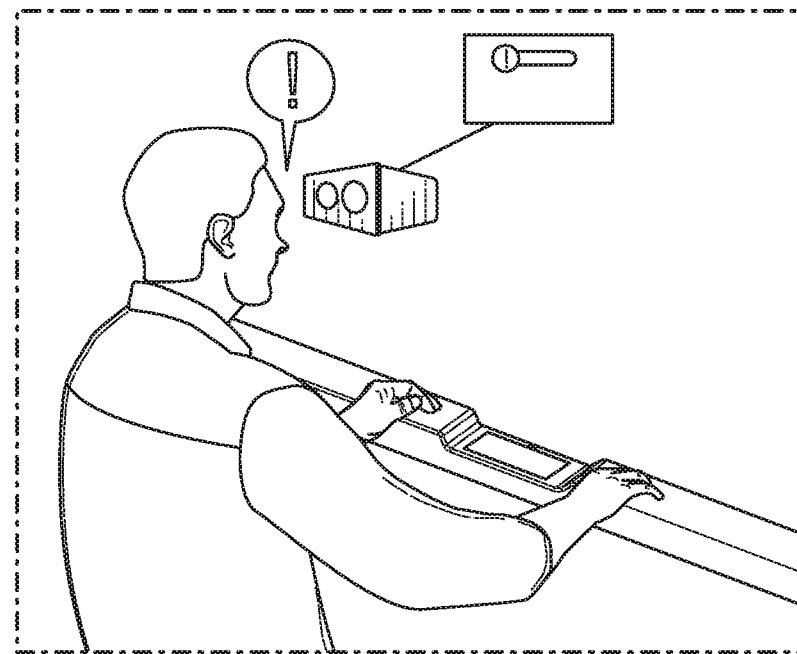
FIG. 29 illustrates an alert that can be displayed in the viewer of a potential collision.
Figure 30:
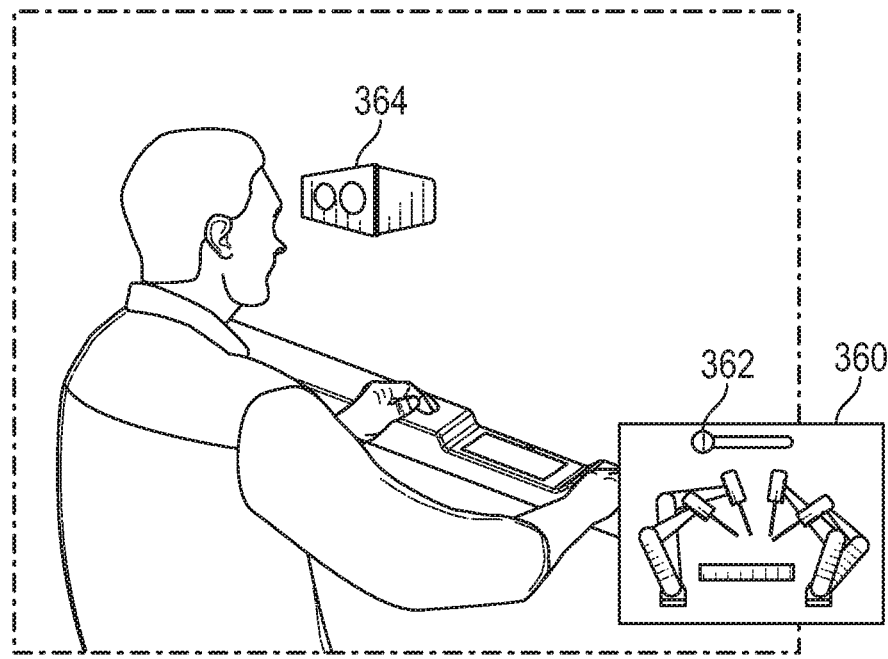
FIG. 30 illustrates a visual rendering of the system that can be displayed in the viewer or on another display when the system is in a collision alert state.

Some aspects of the systems disclosed herein can be configured such that a physician would be alerted within the viewer of a possible collision (such as, for example, when an arm is within a predetermined distance from another object). FIG. 29 illustrates an alert that can be displayed in the viewer of a potential collision. The alert can optionally be audible, visual, or both. In some aspects, when a collision condition exists, the system can be configured to freeze, lock, or slow down one or more of the robotic arms to prevent them from further movement in a collision direction until the collision condition is cleared. Thereafter, the surgeon can investigate the collision condition on a touch screen display outside of the viewer, as illustrated FIG. 30, which illustrates a visual rendering 360 of the system that can be displayed on the viewer or on another display such as the touch screen when the system is in a collision alert state. Optionally, the physician may leave the viewer and master controller and walk over to the patient-side to investigate areas of potential collision, or ask the staff to do so.

Alternatively, the system can be configured such that the system can display a visual representation of the arms and/or other objects that are in a potential collision position within the viewer. For example and without limitation, the system can be configured to display the visual rendering 360 in the viewer 364.

In any aspects, a collision condition can be based on a predetermined distance such that, when any portion, or a designated portion, of a robotic arm is within the predetermined distance from another object, such as another robotic arm or non-robotic arm, the system enters into a collision alert state and/or provides an alert on the viewer.

In related aspects, collisions can cover, e.g., one or more of the following scenarios. In one scenario, the arms/instruments/cameras are physically touching one another or an external object as perceived by force sensors in/in the arms. In another scenario, the arms/instruments/cameras are within a certain trigger or boundary distance of each other. This range may be configurable, dynamic, and/or adapt to what is happening, e.g., during procedure(s). The ability to configure this feature based on the procedure or instrument used would allow for creative applications when doing combined endoscopic and laparoscopic procedures. In further related aspects, the trigger distance may be the critical distance at which the graphic overlay in the viewer alerts an impending collision. In yet further related aspects, the boundary distance may be the critical distance at which the robot stops motion and alerts the physician of a collision, e.g., via the viewer.

In this state, the system can be configured to (i) alert the physician(s) and/or staff of the potential collision and (ii) show the physician(s) and/or the staff a graphical representation of at least the arms or other objects that are in a collision state so that the physician would not have to leave the physician console to troubleshoot the potential collision. The graphical representation depicting collisions can optionally be configured to be interactive or, alternatively, can be configured to be non-interactive. The system can be configured to refresh the visual rendering or graphical representation at predetermined intervals so that the user can see a movement of the one or more robotic arms that are being moved to alleviate the collision condition. The rendering can also be manipulatable so that the surgeon can rotate, pan, zoom into, and/or zoom out of the view for a better understanding of the position of the arms and other objects of the system.

D. Initiation of Instrument Exchange.

Traditionally, if a physician needs to swap an instrument out on any specific arm, she or he must verbally call out to his staff during surgery (e.g., "swap instrument X with instrument Y"). Such an exchange requires the physician and technician to know which instrument is attached to which robotic arm and which arm is which. This can be confusing with drapes over the arms in a dark operating room setting. Such difficulties will be exacerbated when using an even greater number of arms (e.g., six robotic arms), as can be included in any of the aspects disclosed herein.

Any implementations disclosed herein can be configured such that the system can selectively display a graphical rendering to facilitate instrument exchange procedures. The user can selectively cause the system to display an interactive instrument exchange menu, such as the instrument exchange menu 400 shown in FIG. 31. The instrument exchange menu 400 shown in FIG. 31 can show all of the robotic arms that are currently being used in the system and an identification of each instrument that is assigned to or coupled with each of the robotic arms 402. In the system shown in FIG. 31, the system has six robotic arms. An instrument or camera can be coupled with each of the arms, as can be indicated by instrument symbol graphic 406 on the instrument exchange menu. The system can be configured such that the master controller, such as the first or second handle, can be used to move a pointer over the instrument exchange menu to allow the user to select or designate a desired instrument for exchange.

Figure 31:
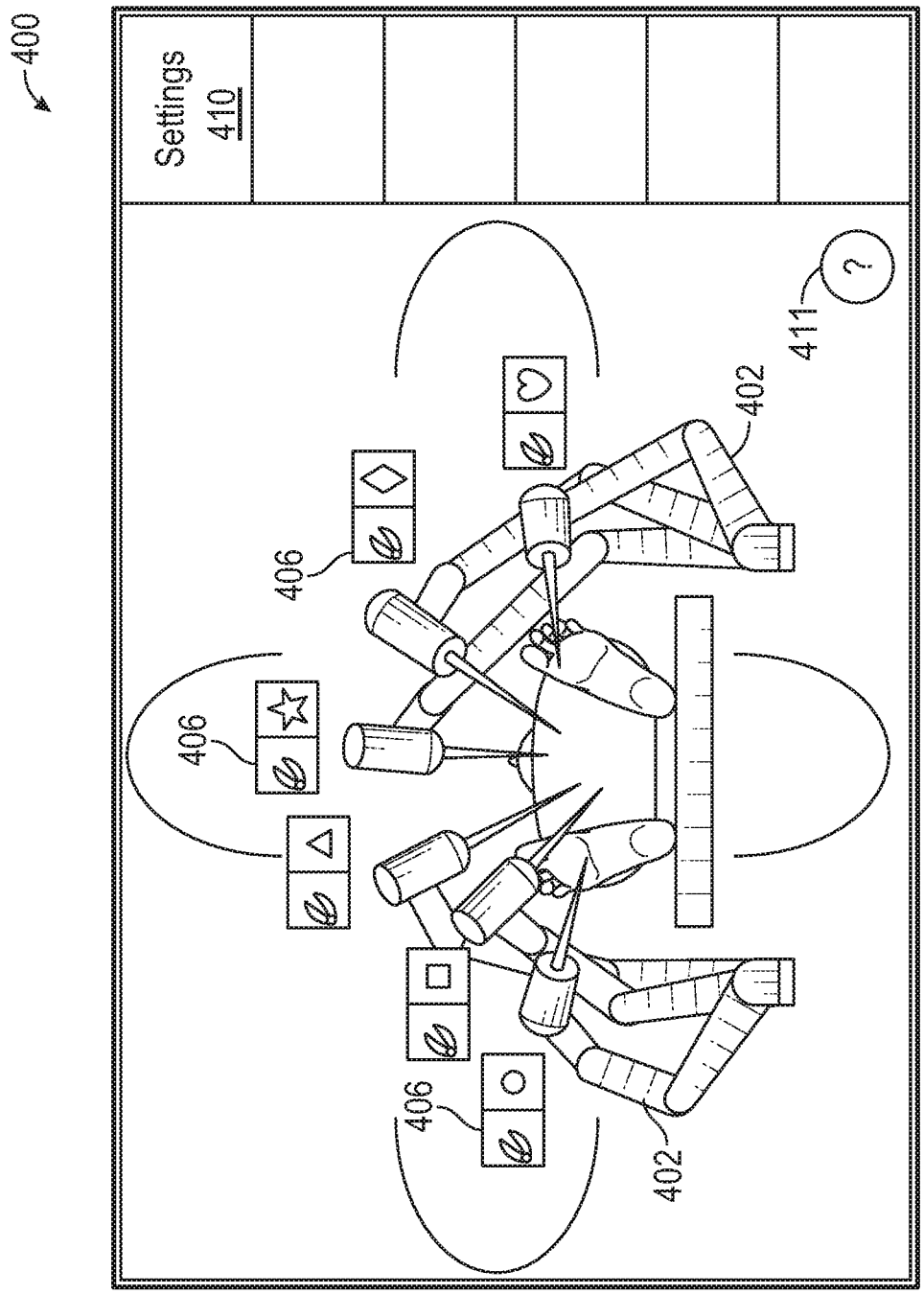
FIG. 31 illustrates an example of an instrument exchange menu that can be displayed on the viewer.

In related aspects, unique identifiers such as symbols, letter, numbers, shapes, colors, and/or other identifiers may be used for the graphical rendering in the viewer (and/or display) to individually identify the arms. For example, as shown in FIG. 31, a circle, a square, a triangle, a star, a diamond, and a heart are used to individually identify the arms. In further related aspects, unique identifiers (e.g., symbols, thumbnails, icons, etc.) may be used next to the arm identifiers (e.g., to the left of the arm identifier) to indicate the type of tool/instrument or camera attached, coupled, or associated with each arm. The symbol/thumbnail may show the type of tool or simply whether a tool (or a camera or nothing) is attached to the arm. The symbol/thumbnail may facilitate providing a visual cue to the physician regarding which instrument is installed on which arm. In yet further related aspects, the menu 400 may include a settings button 410 and/or an icon/button 411 that allows the user to obtain more information or request help regarding the robotic system. In still further related aspects, the menu 400 provides a high level status/summary of the robotic system, wherein the user may use controllers (e.g., gimbals, touchpad, etc.) to: tap to open a panel of detailed status and settings; slide to change the angle of the render; pinch to zoom in or out of the rendering.

In related aspects, a user can select a desired tool and cause the system to prepare the tool/instrument to be unloaded and/or replaced with another tool/instrument. Further, the system can be configured such that the user can unlock or unload a desired or selected tool/instrument from a particular robotic arm so that the tool/instrument can be removed from the robotic arm. Thereafter, the system can be configured to activate a light on the respective arm, in response to a user input, thereby enabling the user to indicate to other members of the surgical team which arm is designated for the instrument exchange. The light can be positioned on or near an end portion of the robotic arm. The master controller (i.e., at least one of the first handle 226 and the second handle 228, which can optionally control a cursor or pointer) can be used to manipulate the instrument exchange menu 400, select the arm for unloading, and/or identify in the instrument exchange menu which instrument will be added to the particular robotic arm following the exchange so that the user can keep track of the instruments on each arm following any exchange procedure.

When a particular arm has been designated for exchange, the system can be configured such that the user can then select a button or other feature, or perform some unique gesture with the master controller such as, optionally, a double click to indicate that the instrument associated with the selected arm is to be replaced. Thereafter, a light or other indicator can be activated on the selected arm so that the other members of the surgical team can perform the exchange procedures.

After a particular arm has been designated for exchange, the visual representation of the arm or a symbol associated with the arm on the interactive menu or graphical overlay can optionally blink, change colors, or provide some other indication that the arm has been designated for exchange. Optionally, the system can be configured such that the light can remain active until the instrument has been exchanged, or for a predetermined period of time, such as 15 seconds, or from approximately 3 seconds to approximately 60 seconds (or more), or from approximately 10 seconds to approximately 30 seconds (or from and to any values within these ranges), after which time the light will deactivate and the instrument will be locked again to the robotic arm if the instrument desired to be exchanged has not been removed. In some aspects, the light on the robotic arm can be configured to blink when the predetermined amount of time has almost been reached, for example within 10% of the predetermined amount of time, or within 10 seconds of the predetermined amount of time.

In any aspects, any of the inputs into the master controller described above (including the double clicking and triple clicking sequences described above) can be used to cause the system to actuate the light on the robotic arm associated with the handle that received the input. For example and without limitation, in some aspects, the user can double-click the master grips of the right hand, causing a light on the corresponding instrument or arm to illuminate for a predetermined period of time (which can be, e.g., 15 seconds, or any of the times ranges disclosed above). As mentioned, the light can show or indicate to the assistant which instrument the user would like removed. Further, the light can show or indicate to the assistant which instrument has been unlocked or unloaded. In some aspects, the system can be configured to extinguish the light after the expiration of the predetermined period of time if no action had been taken or initiated to remove an instrument from the arm having the activated light.

The robotically-enabled medical system of any implementations disclosed herein can optionally include a movable or nonmovable tower (not shown), which can be connected to the console 220 via support cables to provide support for controls, electronics, fluidics, optics, sensors, and/or power to the console 220. Placing such functionality in the tower can allow for a smaller form factor console that may be more easily adjusted and/or re-positioned by an operating physician and his/her staff and can reduce clutter in the operating room, since the tower may be positioned away from the active area within the operating room.

The tower can include component(s) of a computer-based control system that stores computer program instructions, for example, within a non-transitory computer-readable storage medium such as a persistent magnetic storage drive, solid state drive, etc. The execution of those instructions, whether the execution occurs in the tower or the console 220, may control the entire system or any sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower can also be configured to house or support pump(s), flow meter(s), valve control(s), irrigation and aspiration equipment, and/or other components. The tower can also include support equipment for the sensors deployed throughout the robotic system 100. For example, the tower can optionally include opto-electronics equipment for detecting, receiving, and processing data received from the optical sensors or cameras throughout the robotic system, etc. In combination with the control system, such opto-electronics equipment may be used to generate real-time images for display in any number of consoles deployed throughout the system, including in the main viewer in the console that the surgeon uses to perform most of the procedures.

Implementations disclosed herein provide systems, methods and apparatus for performing medical procedures. Any implementations disclosed herein can comprise any combination of the foregoing methods, devices, components, materials, and any other details of the foregoing aspects or aspects of the aspects to form new aspects, all of which are contemplated as being part of this disclosure.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain aspects, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system for a medical procedure, comprising:
a set of one or more robotic arms;
an imaging device coupled to one of the set of one or more robotic arms;
a master controller;
a viewer communicatively coupled with the imaging device and configured to render one or more digital images based on image data from the imaging device;
at least one computer-readable memory having stored thereon executable instructions; and
one or more processors in communication with the at least one computer-readable memory and configured to execute the instructions to cause the system to at least:
in a first mode of operation, cause movement of at least one of the set of one or more robotic arms based on a first user input received at the master controller;
in a second mode of operation, cause the viewer to display an interactive menu and a graphical overlay on the one or more digital images,
wherein a second user input enables a user interaction with the interactive menu, wherein the graphical overlay indicates a current position and orientation of each of the one or more robotic arms, a current position of an object, and an alert identifying an area of potential collision between the one or more robotic arms and the object, and wherein the area of potential collision is based on the object being within a predetermined trigger distance from at least one of the one or more robotic arms; and cause further movement of the one or more robotic arms to be suspended until at least the alert is deactivated by an operator of the system after the alert is displayed and when the object is within a predetermined boundary distance from the at least one of the one or more robotic arms, wherein the predetermined trigger distance is greater than the predetermined boundary distance.

2. The system of claim 1, wherein the one or more processors are further configured to execute the instructions to:

generate a visual rendering of the one or more robotic arms, wherein the visual rendering shows a current position and orientation of each of the one or more robotic arms; and cause the viewer to display the visual rendering.

3. The system of claim 2, wherein the visual rendering:
includes a patient's body; and
shows a current position and orientation of each of the one or more robotic arms relative to the patient's body.

4. The system of claim 1, further comprising a non-robotic arm, wherein the graphical overlay includes a current position and orientation of the non-robotic arm and identification of one or more areas of potential collision between the non-robotic arm and the one or more robotic arms.

5. The system of claim 1, wherein the one or more processors are further configured to execute the instructions to cause the viewer to display the interactive menu at least in part over the one or more digital images, and wherein at least one of the one or more digital images is of a surgical site.

6. The system of claim 1, wherein the one or more processors are further configured to execute the instructions to cause the system to switch from the first mode of operation to the second mode of operation upon a receipt of a double click of a grip of the master controller.

7. The system of claim 1, further comprising one or more foot pedals.

8. The system of claim 7, wherein the one or more processors are further configured to execute the instructions to cause the system to switch from the first mode of operation to the second mode of operation upon a receipt of a simultaneous actuation of a clutch feature on the master controller and a clutch feature on the one or more foot pedals.

9. The system of claim 1, wherein the master controller comprises a first gimbal controller and a second gimbal controller.

10. The system of claim 9, wherein the one or more processors are configured to execute the instructions to:

in the first mode of operation, cause movement of a first robotic arm based on a user input received at the first gimbal controller and cause movement of a second robotic arm based on a user input received at the second gimbal controller; and in the second mode of operation, cause movement of a pointer on the one or more digital images in the viewer based on a user input received in at least one of the first gimbal controller and the second gimbal controller.

11. The system of claim 10, wherein, in the second mode of operation, the one or more processors are further configured to execute the instructions to cause the system to change an association between the master controller and the first robotic arm based on a user input comprising a user interaction with at least one of the interactive menu or the graphical overlay such that, in the first mode of operation, the one or more processors are configured to execute the instructions to cause movement of a first robotic arm based on a user input received at the second gimbal controller.

12. The system of claim 1, wherein the one or more processors are further configured to execute the instructions to determine whether the object is within the predetermined boundary distance from at least one of the one or more robotic arms based on data received from force sensors positioned on the one or more robotic arms.

13. The system of claim 1, wherein the predetermined trigger distance is dynamically configurable to different values during performance of a procedure using the one or more robotic arms, and wherein the predetermined trigger distance is dynamically configurable to different values during the performance of the procedure.

14. A system for surgical procedures, comprising:
a plurality of robotic arms;
a first light coupled to a first robotic arm of the plurality of robotic arms;
a viewer;
a master controller;
at least one computer-readable memory having stored thereon executable instructions; and
one or more processors in communication with the at least one computer-readable memory and configured to execute the instructions to cause the system to at least:

in a first mode of operation, cause a movement of at least one of the plurality of robotic arms based on user input received at the master controller; and in a second mode of operation:
detect that a first instrument coupled to the first robotic arm has been unlocked from the first robotic arm, wherein the first instrument is to be exchanged with a second instrument;

activate the first light based on a user interaction with an element corresponding to the first instrument in a menu received at the master controller for a first period of time when the first instrument remains coupled to and unlocked from the first robotic arm;

after the first period of time, activate a lighting pattern of the first light for a second period of time when the first instrument remains coupled to and unlocked from the first robotic arm;

deactivate the first light after the first instrument is removed from the first robotic arm and the second instrument is coupled to the first robotic arm; and after the second period of time and when the first instrument has not been removed from the first robotic arm:
deactivate the first light; and
lock the first instrument to the first robotic arm.

15. The system of claim 14, wherein the plurality of robotic arms comprises a second light coupled to a second robotic arm, wherein the one or more processors are configured to execute the instructions to cause the system to, in the second mode of operation, activate or deactivate the second light based on a user interaction with the menu.

16. The system of claim 14, wherein the first light is positioned at a distal end of the first robotic arm.

17. The system of claim 14, comprising an imaging device coupled to one of the plurality of robotic arms and communicatively coupled with the viewer, the viewer configured to render one or more digital images based on image data from the imaging device.

18. The system of claim 14, wherein the lighting pattern of the first light comprises at least one of blinking the first light or changing colors of the first light.

19. A method of using a system having a set of one or more robotic arms adapted for a surgical procedure, comprising:
  in a first mode of operation, causing at least one of the set of one or more robotic arms to move in response to a first user input at a master controller;
  viewing one or more digital images rendered on a viewer; wherein:
    the viewer is communicatively coupled with an imaging device;
    the one or more digital images are based on image data from the imaging device; and
    the imaging device is coupled with one of the set of one or more robotic arms;
  causing the viewer to display an interactive menu over at least a portion of the one or more digital images rendered in the viewer in response to a second user input at the master controller;
  changing the system from the first mode of operation to a second mode of operation;
  in the second mode of operation, causing the viewer to display a graphical overlay on the one or more digital images in response to a third user input at the master controller,
    wherein the third user input comprises a user interaction with the interactive menu,
    wherein the graphical overlay indicates a current position and orientation of each of the one or more robotic arms, a current position of an object, and an alert identifying an area of potential collision between the one or more robotic arms and the object, and
    wherein the area of potential collision is based on the object being within a predetermined trigger distance from at least one of the one or more robotic arms; and
  causing further movement of the one or more robotic arms to be suspended until at least the alert is deactivated by an operator of the system after the alert is displayed and when the object is within a predetermined boundary distance from the at least one of the one or more robotic arms, wherein the predetermined trigger distance is greater than the predetermined boundary distance.

20. The method of claim 19, wherein the interactive menu is displayed at least in part over the one or more digital images, and wherein at least one of the one or more digital images is of a surgical site.

* * * * *